US010174086B2

(12) United States Patent
Titball et al.

(10) Patent No.: US 10,174,086 B2
(45) Date of Patent: Jan. 8, 2019

(54) VACCINE

(71) Applicant: University of Exeter, Exeter (GB)

(72) Inventors: Richard W. Titball, Exeter Devon (GB); Sergio Paulo Fernandes Da Costa, Exeter Devon (GB); Claire Naylor, Greater London (GB); Ajit Basak, Greater London (GB)

(73) Assignee: University of Exeter, Exeter (GB)

( * ) Notice: Subject to any disclaimer, the term of this patent is extended or adjusted under 35 U.S.C. 154(b) by 115 days.

(21) Appl. No.: 15/243,409

(22) Filed: Aug. 22, 2016

(65) Prior Publication Data

US 2017/0051023 A1 Feb. 23, 2017

Related U.S. Application Data

(62) Division of application No. 14/354,117, filed as application No. PCT/GB2012/052639 on Oct. 24, 2012, now Pat. No. 9,422,343.

(30) Foreign Application Priority Data

Oct. 25, 2011 (GB) .................................. 1118394.4

(51) Int. Cl.
| | |
|---|---|
| C07H 21/02 | (2006.01) |
| C07H 21/04 | (2006.01) |
| C07K 14/33 | (2006.01) |
| A61K 39/08 | (2006.01) |
| A61K 39/00 | (2006.01) |

(52) U.S. Cl.
CPC .............. *C07K 14/33* (2013.01); *A61K 39/08* (2013.01); *A61K 2039/552* (2013.01); *A61K 2039/575* (2013.01); *A61K 2039/6006* (2013.01)

(58) Field of Classification Search
CPC ......... A61K 38/00; A61K 39/00; C07H 21/00
See application file for complete search history.

(56) References Cited

U.S. PATENT DOCUMENTS

| | | | |
|---|---|---|---|
| 2010/0261884 A1 | 10/2010 | Ainley et al. | |
| 2011/0033501 A1 | 2/2011 | Curtiss et al. | |

FOREIGN PATENT DOCUMENTS

| | | |
|---|---|---|
| WO | 93/23543 | 11/1993 |
| WO | 2008/148166 A1 | 12/2008 |
| WO | 2012/004645 A1 | 1/2012 |
| WO | 2013/061056 A1 | 5/2013 |

OTHER PUBLICATIONS

Intellectual Property Office, Search Report under Section 17(5), Application No. GB1322463.9 dated Jan. 30, 2014, pp. 1-5.
International application No. GB2012/052369 third party observation dated Feb. 14, 2014, pp. 1-24.
International Search Report and Written Opinion for International Application No. PCT/GB2014/053748 dated Apr. 9, 2015, pp. 1-12.
PCT International Search Report and Written Opinion dated Mar. 1, 2013, PCT Application No. PCT/GB2012/052639, 69 pages.
Abildgaard et al., "In Vitro Production of Necrotic Enteritis Toxin B, by NetB-Positive and NetB-Negative Clostridium Perfringens Originating from Healthy and Diseased Broiler Chickens", Veterinary Microbiology, Elsevier BV, NL, vol. 144, No. 1-2, Jul. 29, 2010, pp. 231-235.
Abrami et al., "Plasma Membrane Microdomains Act as Concentration Platforms to Facilitate Intoxication by Aerolysin", The Journal of Cell Biology, vol. 147, No. 1, Oct. 4, 1999, pp. 175-184.
Adams et al., "PHENIX: a comprehensive Python-based system for macromolecular structure solution", Acta Crysta., 2010, pp. 213-221.
Akiba et al., "Crystal Structure of the Parasporin-2 Bacillus thuringiensis Toxin That Recognizes Cancer Cells", J. Mol. Biol., 386, 2009, pp. 121-133.
Battye et al., "iMOSFLM: a new graphical interface for diffraction-image processing with MOSFLM", Acta Cryst., D67, 2011, pp. 271-281.
Bhown et al., "Structural Studies on ε-Prototoxin of Clostridium Perfringens Type D", Location of the Site of Tryptic Scission Necessary for Activation to ε-Toxin, Academic Press, Inc., Biochemical and Biophysical Research Communications, vol. 78, 1977, pp. 1-8.
Bokori-Brown et al., "Clostridium perfringens epsilon toxin H149A mutant as a platform for receptor binding studies", Protein Science, vol. 22, No. 5, May 8, 2013, pp. 650-659.
Bokori-Brown et al., "Molecular basis of toxicity of Clostridium perfringens epsilon toxin", The FEBS Journal 278, 2011, pp. 4589-4601.
Bowie et al., "Deciphering the Message in Protein Sequences: Tolerance to Acid Substitutions", Science, Mar. 16, 1990, pp. 1306-1310.
Chassin, et al., "Pore-forming epsilon toxin causes membrane permeabilization and rapid ATP depletion-mediated cell death in renal collecting duct cells", Am. J. Physiol. Renal Physiol 293, 2007, pp. F927-F937.
Cole et al., "Clostridium perfringens ε-toxin shows structural similarity to the pore-forming toxin aerolysin", Nature Structural & Molecular Biology, vol. 11, No. 8, Aug. 2004, pp. 1-2.
Cooper et al., "Immunization with recombinant alpha toxin partially protects broiler chicks against experimental challenge with Clostridium perfringens", Veterinary Microbiology 133, 2009, pp. 92-97.

(Continued)

*Primary Examiner* — Gary B Nickol
*Assistant Examiner* — Lakia J Jackson-Tongue

(57) ABSTRACT

There is provided a NetB epitope polypeptide comprising at least 10 contiguous amino acids from SEQ ID NO:1 and comprising a mutation in at least one position between amino acids 130 and 297 as compared with the equivalent position in SEQ ID NO:3, the mutation preferably being located within a rim domain, the polypeptide being capable of binding an antibody which binds to SEQ ID NO:1 and having reduced toxicity compared with the toxicity of SEQ ID NO:1. The polypeptide is useful to vaccinate a subject against infection by *Clostridium perfringens*.

20 Claims, 11 Drawing Sheets

Specification includes a Sequence Listing.

(56) References Cited

OTHER PUBLICATIONS

Cooper et al., "Virulence of Clostridium perfringens in an experimental model of poultry necrotic enteritis", Veterinary Microbiology 142, 2010, pp. 323-328.
Crouch et al., "Safety and efficacy of a maternal vaccine for the passive protection of broiler chicks against necrotic enteritis", Avian Pathology, 39:6, Dec. 10, 2010, pp. 489-497.
Davis et al., "MolProbity: all-atom contacts and structure validation for proteins and nucleic acids", Nucleic Acids Research, 2007, vol. 35, Web Server issue W375-W383.
Elmsley et al., "Features and development of Coot", Acta Cryst., 2010. D66, pp. 486-501.
Evans, "Scaling and assessment of data quality", Acta Cryst., 2006, D62, pp. 72-82.
Fernandes Da Costa et al., "Protection against avian necrotic enteritis after immunisation with NetB genetic or formaldehyde", Vaccine 31, 2013, pp. 4003-4008.
Finnie, "Pathogenesis of brain damage produced in sheep by Clostridium perfringens type D epsilon toxin: a review", Aust Vet J, vol. 81, No. 4, Apr. 2003, pp. 219-221.
Gholamiandekhordi et al., "Molecular and phenotypical characterization of Clostridium perfringens isolates from poultry flocks with different disease status", Veterinary Microbiology 113, 2006, pp. 143-152.
Gholamiandekhordi et al., "Quantification of gut lesions in a subclinical necrotic enteritis model", Avian Pathology, Oct. 2007, 36(5), pp. 375-382.
Gill, "Bacterial Toxins: a Table of Lethal Amounts", Microbiological Reviews, vol. 46, No. 1, Mar. 1982, pp. 86-94.
Hunter, et al., "Cloning and Nucleotide Sequencing of the Clostridium perfringens Epsilon-Toxin Gene and Its Expression in *Escherichia coli*", Infection and Immunity, vol. 60, No. 1, Jan. 1992, pp. 102-110.
Ivie et al., "Gene-Trap Mutagenesis Identifies Mammalian Genes Contributing to Intoxication by Clostridium perfringens ε-Toxin", PLoS ONE 6(3), 2011, pp. 1-13.
Kaldhusdal et al., "Necrotic enteritis challenge models with broiler chickens raised on litter: evaluation of preconditions, Clostridium perfringens strains and outcome variables", FEMS Immunology and Medical Microbiology 24, 1999, pp. 337-343.
Keyburn et al., "Alpha-Toxin of Clostridium perfringens Is Not an Essential Virulence Factor in Necrotic Enteritis in Chickens", Infect. Immun. 2006, 74(11):6496, 2006, pp. 1-6.
Keyburn et al., "NetB, a New Toxin That Is Associated with Avian Necrotic Enteritis Caused by Clostridium perfringens", PLoS Pathog 4(2), 2008, pp. 1-11.
Keyburn et al., "NetB, a Pore-Forming Toxin from Necrotic Enteritis Strains of Clostridium Perfringens", Toxins, vol. 2, No. 7, Jul. 2010. pp. 1913-1927.
Keyburn, Anthony L. et al., "Maternal immunization with vaccines containing recombinant NetB toxin partially protects progeny chickens from necrotic enteritis", Veterinary Research 2013, 44:108, pp. 1-7.
Keyburn, Anthony L. et al., "Vaccination with recombinant NetB toxin partially protects broiler chickens from necrotic enteritis", Veterinary Research 2013, 44:54, pp. 1-8.
Knight et al., "In Vitro Tests for the Measurement of Clostridial Toxins, Toxoids and Antisera II. Titration of Clostridium Perfringens Toxins and Antitoxins in Cell Culture", Biologicals, 1990, 18, pp. 263-270.
Kulkarni et al., "A Live Oral Recombinant Salmonella enterica Serovar Typhimurium Vaccine Expressing Clostridium perfringens Antigens Confers Protection against Necrotic Enteritis in Broiler Chickens", Clinical and Vaccine Immunology, vol. 17(2), Feb. 2010, pp. 205-214.
Kulkarni et al., "Immunization of Broiler Chickens against Clostridium perfringens-Induced Necrotic Enteritis", Clin. Vaccine Immunol. 2007, 14(9), pp. 1070-1077.
Kulkarni et al., "Oral immunization of broiler chickens against necrotic enteritis with an attenuated Salmonella vaccine nectar expressing Clostridium perfringens antigens", Vaccine 26, 2008, pp. 4194-4203.
Mackenzie et al., "Analysis of Receptor Binding by the Channel-forming Toxin Aerolysin Using Surface Plasmon Resonance", J. Biol. Chem., 1999, 274, 22604-22609.
Mancheno et al., "Structural Analysis of the Laetiporus sulphureus Hemolytic Pore-forming Lectin in Complex with Sugars", J. Biol. Chem. 2005, 280,.originally published online Feb. 1, 2005, pp. 17251-17259.
Manich et al., "Clostridium perfringens Delta Toxin Is Sequence Related to Beta Toxin, NetB, and Staphylococcus Pore-Forming Toxins, but Shows Functional Differences", PLoS ONE 3(11): e3764, 2008, pp. 1-13.
McCoy et al., "Phaser crystallographic software", J. Appl. Cryst., 40, 2007, pp. 658-674.
McDonel, "Clostridium perfringens Toxins (Type A, B, C, D, E)", Pharmac. Ther. vol. 10, 1980, pp. 617-655.
McDonel, "Toxins of Clostridium Perfringens Types A, B,C, and E", Chapter 22, Pharmacology of Bacterial Toxins, Dorner & Drew, Pergamon Press, 1986, pp. 477-517.
McDonel, "Pharmacology of Bacterial Toxins: Chapter 22: Toxins of Clostridium Perfringens Types A, B, C, D, and E", Dorner & Drew, Pergamon Press, 1986, pp. 477-517.
Minami et al., "Lambda-Toxin of Clostridium perfringens Activates the Precursor of Epsilon-Toxin by Releasing Its N- and C-Terminal Peptides", Microbiol. Immunol., 41(7), 1997, pp. 527-535.
Needleman et al., "A General Method Applicable to the Search for Similarities in the Amino Acid Sequence of Two Proteins", J. Mol. Biol., 48, 1970, pp. 443-453.
Oyston et al., "Production of a non-toxic site-directed mutant of Clostridium perfringens epsilon-toxin which induces protective immunity in mice", Microbiology, vol. 144, No. 2, Feb. 1, 1998, pp. 333-341.
Parker et al., "Structure of the Aeromonas toxin proaerolysin in its water-soluble and membrane-channel states", Nature, vol. 367, Jan. 20, 1994, pp. 1-4.
Payne et al., "The Clostridium perfringens epsilon-toxin", Reviews in Medical Microbiology, 8 (Suppl 1), S28-S30, 1997, pp. 1-3.
Payne et al., "Evaluation of a new cytotoxicity assay for Clostridium perfringens type D epsilon toxin", FEMS Microbiol., 1994 Lett. vol. 116, pp. 161-167.
Pelish et al., "Dominant-negative inhibitors of the Clostridium perfringens epsilon-toxin", Journal of Biological Chemistry, vol. 284, No. 43, Oct. 23, 2009, pp. 29446-29453.
Petit et al., "Clostridium perfringens: toxinotype and genotype", Trends in Microbiology, vol. 7, No. 3, Mar. 1999, pp. 104-110.
Petit et al., "Clostridium perfringens Epsilon Toxin Induces a Rapid Change of Cell Membrane Permeability to Ions and Forms Channels in Artficial Lipid Bilayers", The Journal of Biological Chemistry, vol. 276, No. 19 Issue of May 11, 2001, pp. 15736-15740.
Petit et al., "Clostridium perfringens Epsilon-Toxin Acts on MDCK Cells by Forming a Large Membrane Complex", Journal of Bacteriology, Oct. 1997, pp. 6480-6487.
Rood, "Virulence Genes of Clostridium Perfringens", Anny. Rev. Microbiol., 52, 1998, pp. 333-360.
Sakurai et al., "The Inactivation of Clostridium Perfringens Epsilon Toxin by Treatment With Tetranitromethane an N-Acetylimidazole", Taxicon, vol. 25, No. 3, 1987, pp. 279-284.
Sambrook et al., "Chapter 15: Expression of Cloned Genes in *Escherichia coli*", Molecular Cloning: A Laboratory Manual. Cold Spring Harbor Laboratory Press, 2001, pp. 15.1-15.29.
Sambrook et al., "Protocol 8: Hybridization of Oligonucleotide Probes in Aqueous Solutions: Washing in Buffers Containing Quaternary Ammonium Salts", Molecular Cloning: A Laboratory Manual. Cold Spring Harbor Laboratory Press, 2001, pp. 10.35-10.37.
Sambrook et al., "Protocol 8: Tetracycline as Regulator of Inducible Gene Expression in Mammalian Cells", Molecular Cloning: A Laboratory Manual. Cold Spring Harbor Laboratory Press, 2001, pp. 1-3.

(56) References Cited

OTHER PUBLICATIONS

Savva et al., "Molecular Architecture and Functional Analysis of NetB, a Pore-Forming Toxin from Clostridium Perfringens", Journal of Biological Chemistry, vol. 288, No. 5, Feb. 1, 2013, pp. 3512-3522.
Shimamoto et al., "Changes in Ganglioside Content Affect the Binding of Clostridium perfringens Epsilon-Toxin to Detergent-Resistant Membranes of Madin-Darby Canine Kidney Cells", Microbiol. Immunol., 49(3), 2005, pp. 245-253.
Shortt et al., "An assessment of the in vitro toxicology of Clostridium perfringens type D E-toxin in human and animal cells", Human & Experimental Toxicology, 2000, 19, pp. 108-116.
Smart et al., "Exploiting structure similarity in refinement: automated NCS and target-structure restraints in BUSTER", Acta Cryst., D68, 2012, pp. 368-380.
Song, et al., "Structure of Staphylococcal a-Hemolysin, a Heptameric Transmembrane Pore", Science, New Series, vol. 274, No. 5294, Dec. 13, 1996, pp. 1859-1866.
Songer, "Clostridial Enteric Diseases of Domestic Animals", Clinical Microbiology Reviews, vol. 9(2), Apr. 1996, pp. 216-234.
Studier, "Protein production by auto-induction in high-density shaking cultures", Protein Expression and Purification 41, 2005, pp. 207-234.
Unknown Author, "Biological and Chemical Terrorism: Strategic Plan for Preparedness and Response", Centers for Disease Control and Prevention. Recomendations of the CDC Strategic Planning Workgroup. MMWR 2000; 49(No. RR-4), pp. 1-26.
Worthington et al., "Physical Changes in the Epsilon Prototoxin Molecule of Clostridium perfringens During Enzymatic Activation", Infection and Immunity, Nov. 1977, vol. 18, No. 2, pp. 549-551.
Zekarias et al., "Recombinant Attenuated Salmonella enterica Serovar Typhimurium Expressing the Carboxy-Terminal Domain of Alpha Toxin from Clostridium perfringens Induces Protective Responses against Necrotic Enteritis in Chickens", Clinical and Vaccine Immunology, vol. 15(5), May 2008, pp. 805-816.

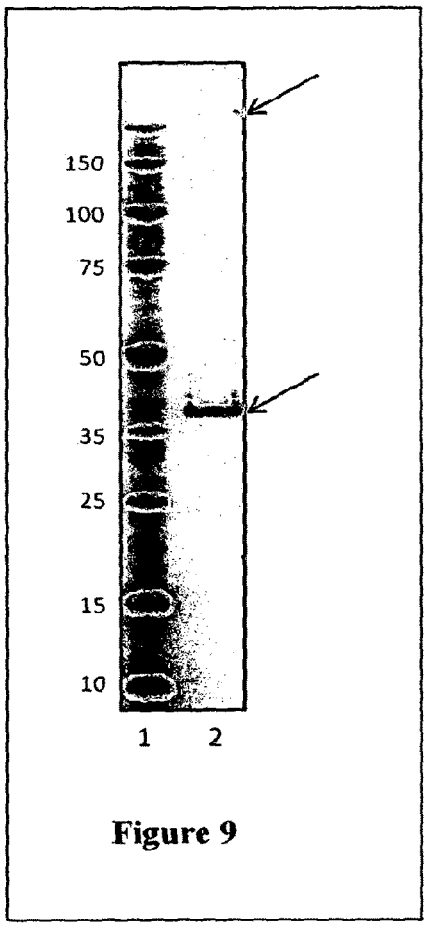
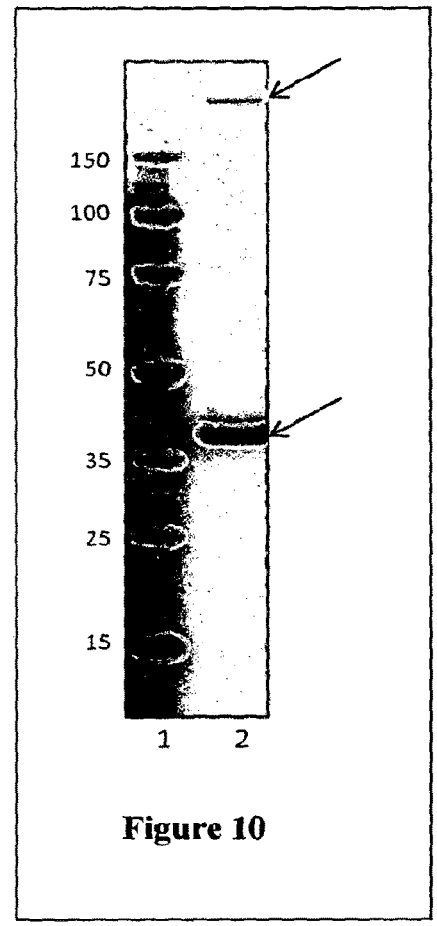
Figure 9
Figure 10

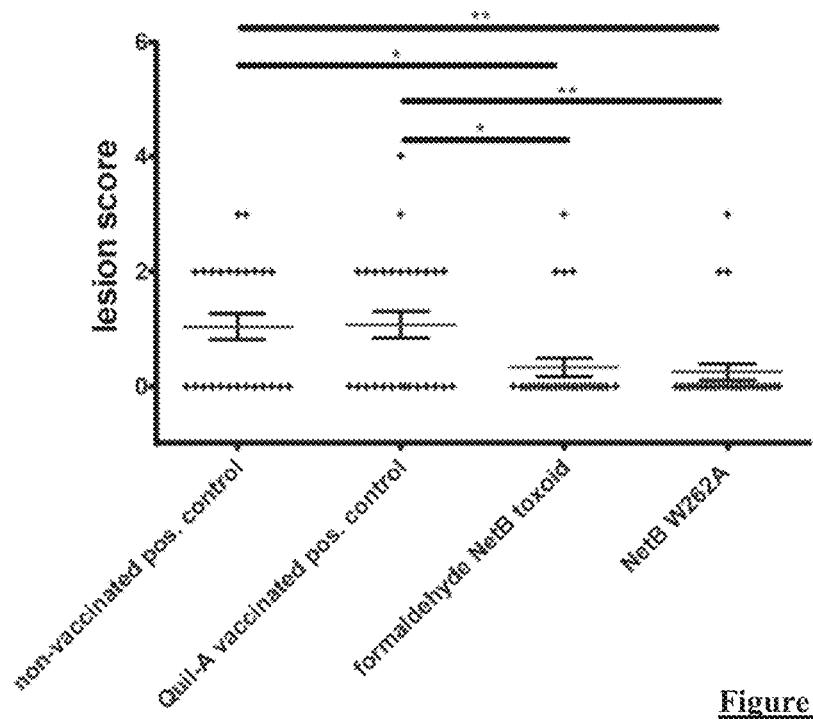
Figure 12
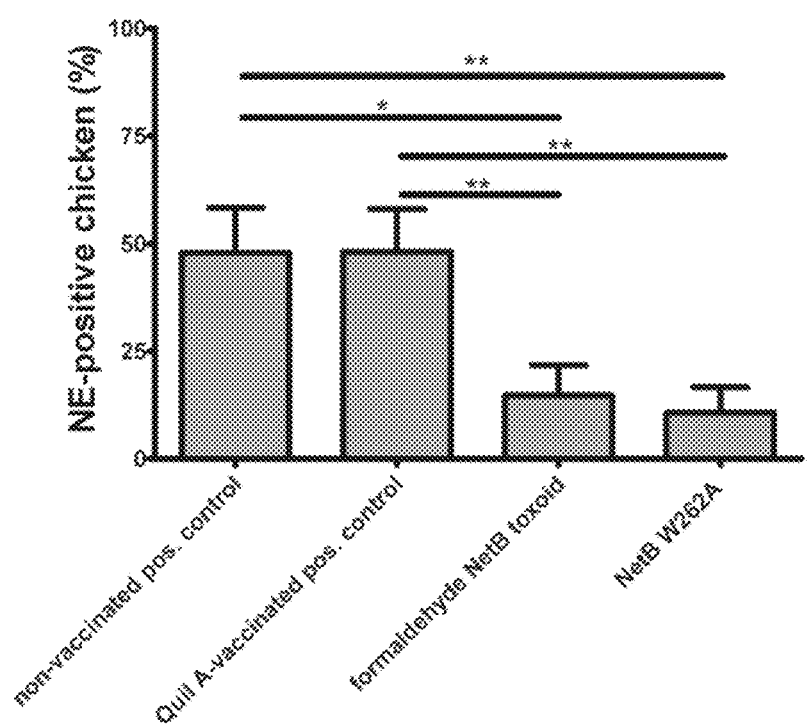

VACCINE

CROSS-REFERENCE TO RELATED APPLICATIONS

This application is a divisional of application Ser. No. 14/354,117, filed Apr. 24, 2014, issuing as U.S. Pat. No. 9,422,243 on Aug. 23, 2016, which is the national stage application of International patent application No. PCT/GB2012/052639, entitled "Vaccine," and filed on Oct. 24, 2012, which claims priority to GB patent application No. 1118394.4, entitled "Vaccine" and filed on Oct. 25, 2011, which are hereby incorporated by reference herein in their entireties.

FIELD OF THE INVENTION

The invention relates to novel polypeptides useful as a vaccine against *Clostridium perfringens*, particularly in chickens and other poultry.

BACKGROUND

*Clostridium perfringens* is an ubiquitous bacterium that can colonise a variety of different biotopes. Due to its anaerobic lifestyle it is not surprising to find *C. perfringens* as a commensal of the normal gut flora in humans and domesticated animals. However, under certain circumstances it is known to be responsible for causing some severe diseases due to its production of a wide range of toxins (Songer (1996) *Clin Microbiol Rev* vol 9: 216-234). Apart from the four toxins used for typing *C. perfringens* (alpha-, beta-, epsilon-, iota-toxin) it is able to produce a selection of non-typing toxins, such as enterotoxin or perfringolysin O (Petit et al., (1999) *Trends Microbiol* vol 7: 104-110). Recently, a novel toxin named NetB (Necrotic enteritis toxin B) has been identified and suggested to play a role in the pathogenesis of avian necrotic enteritis (NE), a severe gastro-intestinal disease that manifests in gross lesions within the intestines of poultry (WO2008/148166). NE is a re-emerging disease that is causing enormous economic costs to the worldwide poultry industry (around 2 billion US dollars per year) (Keyburn et al., (2008) *PLoS Pathog* vol 4: e26). Its re-emergence is due to the initiative of some governments to prohibit the use of antimicrobial growth promoters in animal feed, amongst others to reduce the evolving spread of antibiotic-resistant bacteria in the environment.

The NetB is produced by *C. perfringens* toxinotype A strains and, to a lesser extent, by strains of type C (Kaldhusdal et al. (1999) *FEMS Immunol Med Microbiol* vol 24: 337-343). The protein is 322 amino acids long in its active form and has an estimated molecular weight of 36.5 kDa. Although the molecular basis of toxicity is still little understood, several studies suggest that the NetB is a new member of the small β-pore-forming toxins (β-PFTs) as it is able to form pores on membranes and shares amino acid sequence similarity with several other related members of the small pore-forming toxins family (38% identity with the beta toxin from *C. perfringens*, 40% identity with the *C. perfringens* delta toxin, and 31% identity with the alpha toxin from *S. aureus*) (Keyburn et al. (2008) *PLoS Pathog* vol 4: e26; Manich et al. (2008) *PLoS One* vol 3: e3764). It was initially assumed that the alpha toxin, which is produced by the same bacterium, is the major virulence factor for causing NE, but experiments with an alpha toxin mutant showed that this strain was still virulent and able to cause disease (Keyburn et al. (2006) *Infect Immun* vol 74: 6496-6500). In contrast, a netB mutant was not capable of causing NE, whereas the wild type and the complemented mutant could (Keyburn et al. (2008) *PLoS Pathog* vol 4: e26). However, it is still unsettled as to whether the NetB is the key virulence factor for causing NE, as in some cases it was reported that even *C. perfringens* strains without the netB gene were still capable of virulence (Cooper & Songer (2009) *Vet Microbiol* vol 142: 323-328). Moreover, immunization studies with alpha toxin and other antigens, such as a hypothetical zinc metalloprotease and a pyruvate-ferredoxine oxidoreductase, have been identified to moderately protect chicken from developing NE (Cooper et al. (2009) *Vet Microbiol* vol 133: 92-97; Zekarias et al. (2008) *Clin Vaccine Immunol* vol 15: 805-816; Kulkarni et al. (2010) *Clin Vaccine Immunol* vol 17: 205-214; Kulkarni et al. (2007) *Clin Vaccine Immunol* vol 14: 1070-1077).

The heptameric structure of one of the most widely studied β-PFT, *S. aureus* α-hemolysin (αHL), was determined over 20 years ago (Song L et al. (1996) *Science* vol. 274: 1859-1866) and was, until recently, the only high resolution structure of a β-PFT in the membrane-inserted form. The ring-shaped complex resembles a mushroom with the cap forming the extracellular domain and the stem forming the membrane-spanning region, in which each subunit contributes one β-hairpin. Although NetB appears to form pores in target cell membranes, little is known about the molecular basis for this toxicity which hinders the development of effective control measures against NE.

Several attempts have been made on the development of an effective vaccine to protect chicken against NE but, to date, without significant success.

SUMMARY OF INVENTION

According to a first aspect of the invention, there is provided a NetB epitope polypeptide comprising at least 10 contiguous amino acids from SEQ ID NO:1 and comprising a mutation in at least one position between amino acids 130 to 297 as compared with the equivalent position in SEQ ID NO:3 (or SEQ ID NO:1), the polypeptide being capable of binding an antibody which binds to the polypeptide of sequence SEQ ID NO:1 and having reduced toxicity compared with the toxicity of the polypeptide of sequence SEQ ID NO:1.

This skilled person is readily able to determine "equivalent positions" between two sequences, by aligning sequences to achieve maximum identical amino acids at as many positions as possible, for example by using a global sequence alignment program such as is available via blast.ncbi.nlm nih.gov, discussed further below.

The inventors have made several polypeptides derived from NetB and having at least one mutation in an amino acid position equivalent to the position in wild-type NetB sequence SEQ ID NO:3 (or SEQ ID NO:1) which, surprisingly, have reduced or absent toxicity compared to the toxicity of the mature protein SEQ ID NO:1, which lacks the N-terminal 30 amino acid signal peptide included in SEQ ID NO:3. Therefore, when SEQ ID NOs:1 and 3 are subjected to global sequence alignment with one another, as mentioned above, amino acids 1-292 of SEQ ID NO:1 align exactly with amino acids 31-322 of SEQ ID NO:3. Reference to particular positions in this specification is by comparison to the positions in full-length NetB SEQ ID NO:3, since the skilled person typically numbers the positions of the full-length protein, rather than the mature truncated protein.

The level of toxicity may be determined as described herein, for example by use of a LMH cell-based LDH assay. The polypeptides of the invention provide protection, when administered to a subject such as a chicken, from infection by *Clostridium perfringens*. Such protection may be partial, whereby the probability of an individual subject within a population of becoming infected by *C. perfringens* is reduced, or complete, whereby the subject will not become infected by *C. perfringens* (i.e., the probability of becoming infected is 0%).

The term "NetB epitope polypeptide" as used herein means a polypeptide which comprises one or more (or all) epitopes of mature wild-type NetB, as represented by SEQ ID NO:1. The term "epitope" refers to the amino acids (typically a group of around 5 or more amino acids) within a polypeptide sequence which are essential in the generation of an immune response. These amino acids can be consecutive in the sequence but, more typically, are non-consecutive, grouping together when the tertiary structure of the native protein is formed. Provided that these amino acids are within a polypeptide environment which enables them to form the correct epitopic tertiary structure, they can be used to provide a protective vaccine composition. For example, a NetB epitope polypeptide may be one which is capable of binding to an antibody which binds to the mature wild-type NetB having sequence SEQ ID NO:1.

Preferably, the NetB epitope polypeptide comprises a single mutation in one position between 130-297 as compared with the equivalent position in SEQ ID NO:3. Preferably, the mutation comprises one amino acid substitution to an alanine.

The NetB epitope polypeptide may comprise at least 10 contiguous amino acids from SEQ ID NO:29, preferably including at least 5, 10, 15, 20, 25, 30, 35, 40, 45, 46, 47 or 48 contiguous amino acids from SEQ ID NO:30. SEQ ID NO:29 aligns exactly with amino acids 128-195 of SEQ ID NO:3 and SEQ ID NO:30 aligns exactly with amino acids 138-185 of SEQ ID NO:3, when global sequence alignment analysis is used, as mentioned elsewhere herein.

The amino acid sequence shown as SEQ ID NO:30 is a beta-hairpin structure within the NetB protein, which is believed to unfold into the membrane during insertion of NetB into a membrane to form a beta-barrel pore complex. In this embodiment, the mutation in at least one position as compared with the equivalent position in SEQ ID NO:3 is in at least one of positions 130-190 (equivalent to positions 3 to 63 of SEQ ID NO:29), preferably in at least one of positions 138-185 as compared with SEQ ID NO:3 (positions 11-58 of SEQ ID NO:29 and positions 1-48 of SEQ ID NO:30). The polypeptide may comprise a sequence equivalent to SEQ ID NO:30 which differs from SEQ ID NO:30 only in having at least one amino acid substitution, deletion or addition at one or more positions within the sequence, for example at 1-20 positions or 1-10 positions, preferably at 1, 2, 3, 4 or 5 positions. Therefore, the NetB epitope polypeptide of the invention may comprise an amino acid sequence which is at least about 60%, 70%, 80%, 85%, 89%, 91%, 93%, 95% or at least about 97% identical to SEQ ID NO:30, determined using a global sequence alignment comparison as described elsewhere herein.

In one embodiment, the polypeptide may comprise a mutation at either or both of positions P138 and/or position Y182, numbered as found in SEQ ID NO:3. The polypeptide comprising a mutation at position P138 may be non-toxic. In any embodiment, the amino acid P (Proline) at position 138 and/or Y (Tyrosine) at position 182 may be replaced with amino acid A.

Therefore, the polypeptide according to any preceding claim may comprise the amino acid sequence NTISX-EQPDF (SEQ ID NO:25) and/or SYNVQNTISXEQP DFRTIQR (SEQ ID NO:26), where "X" is any amino acid other than Y. Alternatively or additionally, the polypeptide according to any preceding claim may comprise the amino acid sequence ANSIXKNTID (SEQ ID NO:27) and/or NNI-KIANSIX KNTIDKKDVS (SEQ ID NO:28), where "X" is any amino acid other than P. In any of these embodiments, "X" may be amino acid A (Alanine). The polypeptide comprising SEQ ID NO:27 and/or 28 may be non-toxic.

Alternatively, the NetB epitope polypeptide may comprise at least 10 contiguous amino acids from SEQ ID NO:1 and comprising a mutation in at least one position as compared with the equivalent position in SEQ ID NO:3, the polypeptide being capable of binding an antibody which binds to SEQ ID NO:1 and having reduced toxicity compared with the toxicity of SEQ ID NO:1, the polypeptide comprising a β-sandwich domain, a rim domain and a stem domain, wherein the at least one mutation is located in the rim domain. Preferably, the mutation is a conserved residue in the rim domain.

In one embodiment, the NetB epitope polypeptide may comprise at least 10 contiguous amino acids from SEQ ID NO:34, preferably including at least 5, 10, 15, 20, 25, 30, 35, 40, 45, 46, 47 or 48 contiguous amino acids from SEQ ID NO:35. SEQ ID NO:34 aligns exactly with amino acids 212-297 of SEQ ID NO:3 and SEQ ID NO:35 aligns exactly with amino acids 217-292 of SEQ ID NO:3, when global sequence alignment analysis is used, as mentioned elsewhere herein.

The polypeptide may comprise a sequence equivalent to SEQ ID NO:35 which differs from SEQ ID NO:35 only in having at least one amino acid substitution, deletion or addition at one or more positions within the sequence, for example at 1-20 positions or 1-10 positions, preferably at 1, 2, 3, 4 or 5 positions. Therefore, the NetB epitope polypeptide of the invention may comprise an amino acid sequence which is at least about 60%, 70%, 80%, 85%, 89%, 91%, 93%, 95% or at least about 97% identical to SEQ ID NO:35, determined using a global sequence alignment comparison as described elsewhere herein.

In another embodiment, the polypeptide may comprise a mutation at one or more of positions Y221, R230, W287 and/or position W292, numbered as found in SEQ ID NO:3, preferably being a mutation at position W292. In any embodiment, the amino acid at position 221, 230, 287 or 292 may be replaced with amino acid A.

Therefore, the polypeptide may comprise the amino acid sequence YHAIXGNQLF (SEQ ID NO:40) and/or YNIDSYHAIXGNQLFMKSRL (SEQ ID NO:41), where "X" is any amino acid other than Y. Alternatively or additionally, the polypeptide may comprise the amino acid sequence FMKSXLYNNG (SEQ ID NO:42) and/or YGN-QLFMKSXLYNNGDKNFT (SEQ ID NO:43), where "X" is any amino acid other than R. In another embodiment, the polypeptide may comprise the amino acid sequence YIL-NXETTQW (SEQ ID NO: 44) and/or RFDNDYILNX-ETTQWRGTNK (SEQ ID NO: 45), where X is any amino acid other than W. In a preferred embodiment, the polypeptide comprises the amino acid sequence ETTQXRGTNK (SEQ ID NO: 46) and/or YILNWETTQXRGTNKLSSTS (SEQ ID NO: 47), where X is any amino acid other than W. In any of these embodiments, "X" may be amino acid A (Alanine). The polypeptide comprising any of the aforementioned sequences may be non-toxic.

The polypeptide according to the invention may form part of a fusion protein. The polypeptide may have at least about 60% sequence identity to SEQ ID NO:1, for example, about 65%, 70%, 75%, 80%, 85%, 90%, 91%, 92%, 93%, 94%, 95%, 96%, 97%, 98% or about 99% sequence identity to SEQ ID NO:1. Sequence identity may be determined using the Needleman-Wunsch Global Sequence Alignment Tool available from the National Center for Biotechnology Information (NCBI), Bethesda, Md., USA, for example via blast.ncbi.nlm nih.gov, using default parameter settings. When comparing the level of sequence identity to SEQ ID NO:1, this typically should be done relative to the whole length of SEQ ID NO:1, to avoid short regions of high identity overlap resulting in a high overall assessment of identity (i.e., a global alignment method is used). For example, a short polypeptide fragment having, for example, five amino acids might have a 100% identical sequence to a five amino acid region within the whole of SEQ ID NO:1, but this does not provide a 100% amino acid identity unless the fragment forms part of a longer sequence which also has identical amino acids at other positions equivalent to positions in SEQ ID NO:1.

An epitope polypeptide according to the invention may be, as mentioned above, any which comprises at least one epitope of NetB and is capable of binding an antibody which will bind to a polypeptide having sequence SEQ ID NO:1. Therefore, the polypeptide may be as little as about 20 amino acids in length provided that it still binds to such an antibody, for example, it may be at least about 30, 40, 50, 70, 90, 120, 150 or about 170 amino acids in length. In some embodiments, the polypeptide may be at least about 190 amino acids in length, for example, it may be between 190 and 360 amino acids in length, such as between 200-350, 220-340 or 250-310 in length. In some embodiments, the polypeptide may be at least about 200 amino acids in length, for example, at least about 220, 230, 240, 250, 260, 270, 280 or about 290 amino acids in length. In certain specific embodiments, the polypeptide may be 292 amino acids in length.

In one embodiment, the polypeptide according to the invention has amino acid sequence SEQ ID NO:5. In another embodiment, it has amino acid sequence SEQ ID NO:6. In further embodiments, the polypeptide according to the invention is selected from one of the amino acid sequences SEQ ID NOs: 36, 37, 38 or 39.

The present invention also encompasses polypeptides comprising variants of the epitope polypeptides and methods utilising these variant polypeptides. As used herein, a "variant" means a polypeptide in which the amino acid sequence differs from the base sequence from which it is derived in that one or more amino acids within the sequence are substituted for other amino acids. The variant is a functional variant, in that the functional characteristics of the polypeptide from which the variant is derived are maintained. For example, the variant polypeptide may have a similar ability to bind an antibody capable of binding to a non-variant polypeptide (such as, by way of non-limiting example, SEQ ID NOs:5, 6, 36, 37, 38 or 39). In particular, any amino acid substitutions, additions or deletions must not alter or significantly alter the tertiary structure of one or more epitopes contained within the polypeptide from which the variant is derived, so that the variant polypeptide retains the ability to bind to an antibody which binds to SEQ ID NO:1. The skilled person is readily able to determine appropriate functional variants and to determine the tertiary structure of an epitope and any alterations thereof, without the application of inventive skill.

Amino acid substitutions may be regarded as "conservative" where an amino acid is replaced with a different amino acid with broadly similar properties. Non-conservative substitutions are where amino acids are replaced with amino acids of a different type.

By "conservative substitution" is meant the substitution of an amino acid by another amino acid of the same class, in which the classes are defined as follows:

| Class | Amino acid examples |
| --- | --- |
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His. |

As is well known to those skilled in the art, altering the primary structure of a polypeptide by a conservative substitution may not significantly alter the activity of that polypeptide because the side-chain of the amino acid which is inserted into the sequence may be able to form similar bonds and contacts as the side chain of the amino acid which has been substituted out. This is so even when the substitution is in a region which is critical in determining the polypeptide's conformation.

As mentioned above, non-conservative substitutions are possible provided that these do not disrupt the tertiary structure of an epitope within the polypeptide, for example, which do not interrupt the immunogenicity (for example, the antigenicity) of the polypeptide.

Broadly speaking, fewer non-conservative substitutions will be possible without altering the biological activity of the polypeptide. As mentioned above, variants may suitably be at least about 60% identical to the base sequence.

Sequence identity between amino acid sequences can be determined by comparing an alignment of the sequences. When an equivalent position in the compared sequences is occupied by the same amino acid, then the molecules are identical at that position. Scoring an alignment as a percentage of identity is a function of the number of identical amino acids at positions shared by the compared sequences. When comparing sequences, optimal alignments may require gaps to be introduced into one or more of the sequences, to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties. As mentioned above, the percentage sequence identity may be determined using the Needleman-Wunsch Global Sequence Alignment tool, publicly available via blast.ncbi.nlm nih.gov, using default parameter settings. The Needleman-Wunsch algorithm was published in J. Mol. Biol. (1970) vol. 48:443-53.

According to a second aspect of the invention, there is provided a polynucleotide having a nucleic acid sequence which encodes for a polypeptide according to the first aspect of the invention, or the complement of such a polynucleotide. Such a polynucleotide may comprise, for example, SEQ ID NOs:31 and/or 32, encoding SEQ ID NOs:5 and 6, respectively or SEQ ID NOs: 48, 49, 50 and/or 51 encoding SEQ ID NOs: 36, 37, 38 and 39 respectively. The invention also encompasses variant nucleic acids encoding the polypeptides of the invention. The term "variant" in relation to a nucleic acid sequence means any substitution of, variation of, modification of, deletion of, or addition of one or more nucleic acid(s) from or to a polynucleotide sequence, providing the resultant polypeptide sequence encoded by the polynucleotide exhibits at least the same properties as the polypeptide encoded by the basic sequence. The term therefore includes allelic variants and also includes a polynucleotide (a "probe sequence") which substantially hybridises to the polynucleotide sequence of the present invention. Such hybridisation may occur at or between low and high stringency conditions. In general terms, low stringency conditions can be defined as hybridisation in which the washing step takes place in a 0.330-0.825 M NaCl buffer solution at a temperature of about 40-48° C. below the calculated or actual melting temperature ($T_m$) of the probe sequence (for example, about ambient laboratory temperature to about 55° C.), while high stringency conditions involve a wash in a 0.0165-0.0330 M NaCl buffer solution at a temperature of about 5-10° C. below the calculated or actual $T_m$ of the probe sequence (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridisation of nucleic acid sequences have been described for example in Sambrook et al. (2001; "Molecular Cloning: a laboratory manual", $3^{rd}$ Edition, Cold Spring Harbor Laboratory Press, New York).

A related aspect of the invention provides a vector comprising a polynucleotide according to the second aspect of the invention and therefore includes recombinant constructs comprising one or more of the nucleic acid molecules described above. The constructs comprise a vector, such as a plasmid or viral vector, into which a nucleic acid molecule of the invention has been inserted, in a forward or reverse orientation. In a preferred aspect of this embodiment, the construct further comprises regulatory sequences, including, for example, a promoter operably linked to the sequence. Large numbers of suitable vectors and promoters are known to those of skill in the art and are commercially available. Appropriate cloning and expression vectors for use with prokaryotic and eukaryotic hosts are also described in Sambrook, et al.

According to a third aspect of the invention, there is provided a cell comprising a polypeptide and/or a polynucleotide and/or a vector according to preceding aspects. For example, a suitable cell may be a *Salmonella* cell, such as a *Salmonella enterica* cell, in some embodiments from the serovar *typhimurium*. The *Salmonella* may be an attenuated strain. Strains χ8914 and χ9241 may optionally be employed. Such cells are particularly useful to act as vectors when the polypeptide, polynucleotide and vector of the invention is to be used to provide a vaccine for chickens, to reduce the probability that they will be susceptible to infection by *Clostridium perfringens*. For example, such a system is described in Kulkarni et al. (2008, Vaccine vol. 26: 4194-4203).

According to a fourth aspect of the invention, there is provided a subunit vaccine comprising a polypeptide according to the first aspect of the invention. For example, this may be in the form of a fusion protein and/or in the form of a recombinant viral vaccine.

A fifth aspect of the invention provides a vaccine composition comprising a polypeptide and/or a polynucleotide and/or a vector and/or a cell and/or a subunit vaccine according to preceding aspects of the invention. The composition may further comprise excipients and/or diluents appropriate for the means by which the composition is to be administered to a subject in need of vaccination against infection by *C. perfringens*. Selection of appropriate components is within the routine capability of the skilled person without the application of inventive activity.

For example, the vaccine composition of the invention may conveniently be formulated using a pharmaceutically acceptable excipient or diluent, such as, for example, an aqueous solvent, non-aqueous solvent, non-toxic excipient, such as a salt, preservative, buffer and the like. Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Preservatives include antimicrobial, anti-oxidants, chelating agents and inert gases. The pH and exact concentration of the various components the vaccine composition are adjusted according to routine skills.

Optionally, the vaccine formulation may include a carrier. Commonly used carrier molecules are bovine serum albumin (BSA), keyhole limpet hemocyanin (KLH), ovalbumin, mouse serum albumin, rabbit serum albumin and the like. Synthetic carriers may be used and are readily available. Means for conjugating peptides to carrier proteins are well known in the art and include glutaraldehyde, m-maleimido-benzoyl-N-hydroxysuccinimide ester, carbodiimide and bis-biazotized benzidine.

In certain situations, it may also be desirable to formulate the vaccine composition to comprise an adjuvant to enhance the immune response. Such adjuvants include all acceptable immunostimulatory compounds such as, for example, a cytokine, toxin, or synthetic composition. Commonly used adjuvants include aluminium hydroxide, aluminium phosphate, calcium phosphate, Freund's adjuvants and Quil-A saponin. In addition to adjuvants, it may be desirable to co-administer biologic response modifiers (BRM) with the peptide or variant or derivative to down regulate suppressor T cell activity.

Possible vehicles for administration of the vaccine formulation include liposomes. Liposomes are microscopic vesicles that consist of one or more lipid bilayers surrounding aqueous compartments. Liposomes are similar in composition to cellular membranes and, as a result, liposomes generally can be administered safely and are biodegradable. Techniques for preparation of liposomes and the formulation (e.g., encapsulation) of various molecules, including peptides and oligonucleotides, with liposomes are well known.

Depending on the method of preparation, liposomes may be unilamellar or multilamellar and can vary in size with diameters ranging from 0.02 μm to greater than 10 μm. Liposomes can also adsorb to virtually any type of cell and then release the encapsulated agent. Alternatively, the liposome fuses with the target cell, whereby the contents of the liposome empty into the target cell. Alternatively, an absorbed liposome may be endocytosed by cells that are phagocytic. Endocytosis is followed by intralysosomal degradation of liposomal lipids and release of the encapsulated agents. In the present context, the polypeptide according to the invention can be localized on the surface of the liposome, to facilitate antigen presentation without disruption of the liposome or endocytosis. Irrespective of the mechanism or delivery, however, the result is the intracellular disposition of the associated polypeptide.

Liposomal vectors may be anionic or cationic. Anionic liposomal vectors include pH sensitive liposomes which disrupt or fuse with the endosomal membrane following endocytosis and endosome acidification. Cationic liposomes are preferred for mediating mammalian cell transfection in vitro, or general delivery of nucleic acids, but are used for delivery of other therapeutics, such as peptides.

Other suitable liposomes that are used in the methods of the invention include multilamellar vesicles (MLV), oligolamellar vesicles (OLV), unilamellar vesicles (UV), small unilamellar vesicles (SUV), medium-sized unilamellar vesicles (MIN), large unilamellar vesicles (LUV), giant unilamellar vesicles (GUV), multivesicular vesicles (MVV), single or oligolamellar vesicles made by reverse-phase evaporation method (REV), multilamellar vesicles made by the reverse-phase evaporation method (MLV-REV), stable plurilamellar vesicles (SPLV), frozen and thawed MLV (FATMLV), vesicles prepared by extrusion methods (VET), vesicles prepared by French press (FPV), vesicles prepared by fusion (FUV), dehydration-rehydration vesicles (DRV), and bubblesomes (BSV). Techniques for preparing these liposomes are well known in the art.

Other forms of delivery particle, for example, microspheres and the like, also are contemplated for delivery of the peptide epitopes or polyepitopes.

Alternatively, nucleic acid-based vaccines may be produced that comprise nucleic acid, such as, for example, DNA or RNA, encoding the immunologically active peptide epitope or polyepitope and cloned into a suitable vector (e.g., vaccinia, canarypox, adenovirus, or other eukaryotic virus vector).

Alternatively, the polypeptide may be administered in the form of a cellular vaccine via the administration of autologous or allogeneic APCs or dendritic cells that have been treated in vitro so as to present the peptide on their surface. *Salmonella* cells may also be used, especially for administration to chickens. This involves the use of live attenuated *Salmonella* vaccines to deliver the antigen. This approach offers a number of advantages. First, live *Salmonella* vaccines can be given orally (the natural route of infection), enabling a non-invasive route of vaccine administration. Second, both mucosal and systemic immune responses can be elicited, which may be important for protection against infection. In addition, live attenuated *Salmonella* vaccines are able to simulate both humoral and cellular immune responses that may be important for protection against disease. Finally, since *Salmonella* is genetically tractable, recombinant *Salmonella* vaccines are relatively easy to develop and are also relatively cost effective to produce.

One of the most widely studied classes of attenuated *Salmonella* used as carriers of foreign antigens are auxotrophs. For example, genetically defined mutants of the aroA gene, encoding 5-enolpyruvylshikimate-3-phosphate synthase, have been constructed in both *S. enterica* var. *Typhimurium* and var. *Typhi*. These mutants are attenuated and immunogenic in mice. Examples of other auxotrophic mutants include *Salmonella* with deletions in the genes involved in the purine biosynthetic pathway. Another well-studied group of attenuated *Salmonella* are mutants that have defined deletions in genes involved in the regulation of *Salmonella* virulence. For example, mutations in genes encoding adenylate cyclase (cya) and camp receptor protein (crp) affect the expression of genes involved.

In one embodiment, the vaccine composition may be included in an animal feed (i.e., a foodstuff suitable for consumption by an animal, particularly a chicken) comprising a polypeptide and/or a polynucleotide and/or a vector and/or a cell and/or a subunit vaccine and/or vaccine composition according to preceding aspects of the invention. This may, in non-limiting examples, be in the form of pellets, crumbs or a mash which may further comprise, again for example only, grain, grass and/or protein components. The composition may also be included in drinking liquids and/or administered via a spray into the atmosphere surrounding the animal which is, consequently, inhaled by the animal.

In a sixth aspect of the invention, a polypeptide and/or a polynucleotide and/or a vector and/or a cell and/or a subunit vaccine and/or a vaccine composition according to any preceding aspect is for use in a method of vaccinating a subject against infection by *Clostridium perfringens*.

Likewise, a seventh aspect of the invention provides a method of vaccinating a subject against infection by *Clostridium perfringens* comprising administering to the subject a protective amount of a polypeptide and/or a polynucleotide and/or a vector and/or a cell and/or a subunit vaccine and/or a vaccine composition according to any preceding aspect. A "protective amount" is an amount sufficient to induce an immune response in the subject, such that the probability of the subject becoming infected by *C. perfringens* if exposed to the bacterium is reduced or removed. For example, antibodies capable of binding to SEQ ID NO:1 may be detectable after the administration, where such antibodies were not detectable prior to the administration, or only detectable at lower concentrations than after administration.

In the sixth and seventh aspects, the subject may be of the genus *Gallus*, for example, of the species *Gallus gallus* (i.e., the domestic chicken). When the subject is a chicken, the preferred means for delivery of the polypeptide and/or a polynucleotide and/or a vector and/or a cell and/or a subunit vaccine of the other aspects of the invention may be a *Salmonella*-based system as described herein. The subject may also be a mammalian subject, for example, a human.

According to an eighth aspect of the invention, there is provided a kit comprising a polypeptide and/or a polynucleotide and/or a vector and/or a cell and/or a subunit vaccine and/or a vaccine composition according to any of the preceding aspects. For example, the kit may be a kit for use by a veterinarian or farmer to vaccinate a flock of chickens and may comprise a *Salmonella* vector comprising a polypeptide according to the invention, for example for administration to chickens by inclusion in their feed.

BRIEF DESCRIPTION OF FIGURES

Embodiments of the invention will be described, by way of example only, with reference to the following FIGS. 1-12 in which:

FIG. 9 shows an SDS PAGE gel of a purified NetB mutant W292A in lane 2, with lane 1 being marker, the arrows indicating monomeric and heptameric forms of NetB (molecular mass is indicated in kDa at the site);

FIG. 10 shows an SDS PAGE gel of wild type NetB in lane 2, with lane 1 being marker, the arrows indicating monomeric and heptameric forms of NetB (molecular mass is indicated in kDa at the site);

FIG. 12 shows the lesion scores of individual animals (top) and percentage NE positive chickens (bottom) after vaccination of animals with a formaldehyde NetB toxoid or NetB W262A.

EXAMPLES

Bacterial Strains and Plasmids

Bacterial strains and plasmids used in this study are listed in Table 1.

TABLE 1

Bacterial strains and plasmids used in this study

| Bacterial strains and plasmids | Relevant genotype or phenotype | Source |
|---|---|---|
| *E. coli* TOP10 | F-mcrA Δ(mrr-hsdRMS-mcrBC) Φ80lacZΔM15 ΔlacX74 recA1 araD139 Δ(araleu) 7697 galU galK rpsL (StrR) endA1 nupG | Invitrogen |
| *C. perfringens* strain 56 | wild-type, virulent NE isolate | (Gholamiandekhordi et al. (2006) *Vet Microbiol* vol 113: 143-152) |
| pCR4-TOPO | kan, bla | Invitrogen |
| pCR4-TOPO-netB | netB | This study |
| pBAD | araBAD promoter, bla | Invitrogen |
| pBAD-netB | netB | This study |

The pBAD vector (Invitrogen) was used as an expression vector and *E. coli* Top10 (Invitrogen) was used as an expression host. The pCR4-TOPO cloning vector (Invitrogen) was used as an intermediate vector to facilitate cloning the genes of interest. *C. perfringens* strain 56 (Gholamiandekhordi et al. (2006) *Vet Microbiol* vol 113: 143-152) was used for amplification of the netB gene. *C. perfringens* was grown anaerobically at 37° C. in brain heart infusion (BHI) broth. *E. coli* strains were grown either in terrific broth (TB) or Luria-Bertani (LB) agar supplemented with ampicillin (100 μg/ml) and grown at 37° C.

Molecular Cloning of netB

Bacterial genomic DNA from *C. perfringens* strain 56 was isolated with the Wizard Genomic Purification Kit (Promega) and used as a template to amplify the encoding region of the netB gene (GenBank accession number: A8ULG6; SEQ ID NO:4) using the following primers:

```
netB_fwd:
                                       (SEQ ID NO: 7)
5'-CCCGGGCTCGAGAGTGAATTAAATGACATAAAC-3' netB_rev:
                                       (SEQ ID NO: 8)
5'-CCCGGGAAGCTTTTACAGATAATATTCTATTTTATG-3'
```

Thereby, the netB was amplified from SEQ ID NO:33, lacking the N-terminal signal sequence (30 amino acids). XhoI and HindIII were used as restriction endonucleases and included in the primers for subcloning into the pBAD bacterial expression vector (underlined in the sequences above). The amplified fragments were first cloned into a pCR4-TOPO cloning vector and verified by sequencing. These fragments were then cloned into the pBAD vector to generate recombinant pBAD-netB and used to transform *E. coli* TOP10 competent cells. Thereby, the recombinant netB is expressed as a 331 amino acids protein (SEQ ID NO:2, having a calculated molecular mass of 38 kDa), containing the mature NetB protein (SEQ ID NO:1) without the native signal peptide and also containing a His-tag and a X-press motif for purification and specific detection of the protein.

Expression and Purification of Recombinant NetB in *E. coli*

The recombinant *E. coli* carrying the pBAD-netB vector was grown to an optical density (OD) of 0.5 and expression was induced for 6 h by adding arabinose at a final concentration of 0.02%. Bacterial cells were harvested by centrifugation and cell lysis was achieved by using BugBuster reagent (Novagen). Recombinant NetB protein was purified by His-bind chromatography columns (GE Healthcare) according to the manufacturer's instructions. Subsequently, the protein was dialysed into Tris-buffered saline (TBS) by using PD-10 desalting columns (GE Healthcare) and protein concentrations were measured with a UV-Vis spectrophotometer (Pierce).

SDS-PAGE and Western Blotting

The protein yield and purity was analysed by SDS-PAGE on precast 4-12% acrylamide-bisacrylamide gels (Novagen). Therefore, gels were run in MES running buffer (Novagen) for about 45 min at 200V and stained with SimplyBlue Safestain (Invitrogen). The perfect protein marker (Novagen) was used as a protein standard. Protein specificity was determined by Western blotting. Therefore, proteins were transferred after electrophoretic separation onto a nitrocellulose membrane with an iBlot dry blotting system (Invitrogen) and blots were developed using primary anti-Xpress specific antibodies (Invitrogen) followed by a secondary anti-mouse antibody conjugated to horseradish peroxidase (HRP). Visualisation was performed with the Amersham ECL Western blotting detection reagents (GE Healthcare) and photographic films were exposed to varying time periods. The precision plus protein WesternC (Biorad) was used as a protein standard.

The results are shown in FIG. 1 (SDS-PAGE) and FIG. 2 (Western blot). The images show monomeric (≈38 kDa) and heptameric (≈266 kDa) forms of the protein.

Cytotoxicity Assay for Effect of rNetB on LMH Cells

Cytotoxicity was measured using a kit (i.e., CYTOTOX96® kit; Promega), in which cytotoxicity is measured as the amount of LDH (lactate dehydrogenase) released from the cell cytosol into the medium caused by the presence of the tested pore-forming cytotoxic compound. The rNetB was evaluated for its cytotoxicity by incubation with chicken hepatocellular carcinoma (LMH; ATTC: CRL-2117) cells, a cell line known to be susceptible for the toxin.

Figure 1:
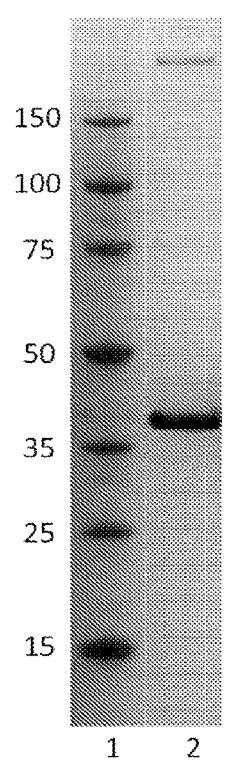
FIG. 1 shows an SDS PAGE gel of a purified recombinant NetB (rNetB) in lane 2, with lane 1 being marker (molecular mass is indicated in kDa at the site)
Figure 2:
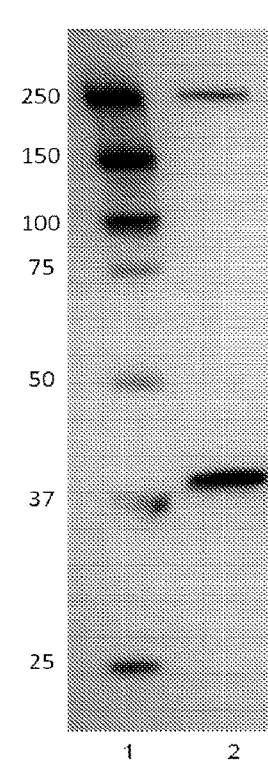
FIG. 2 shows a Western Blot of rNetB with α-Xpress antibodies in lane 2, with lane 1 being marker (molecular mass is indicated in kDa at the site)
Figure 3:
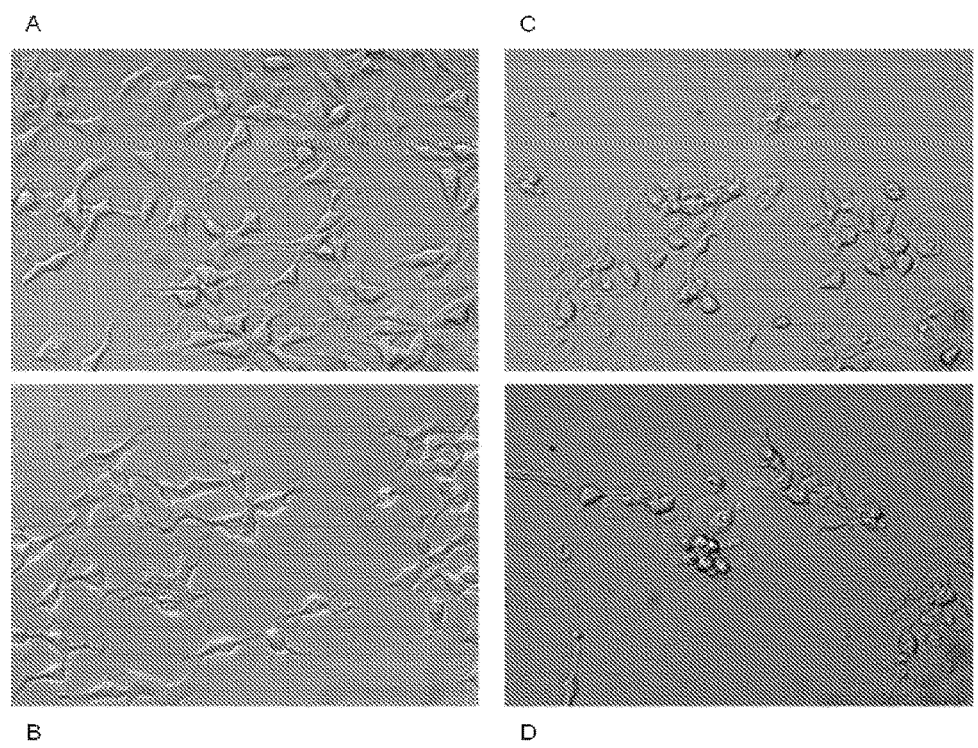
FIG. 3 shows phase-contrast microscopy images showing morphological damage of LMH cells induced by incubation with rNetB, with panels A and B being control cells and panels C and D showing cells exposed to rNetB ($7.7^{-10}$ mol, 1 h), in which cell swelling and cell blebbing induced by rNetB can be observed.

Therefore, LMH cells were grown in Waymouth's MB 752/1 medium (Invitrogen) supplemented with 10% fetal calf serum at 37° C. in a 5% $CO_2$ incubator to 70-80% confluency in 96-well plates. FIG. 3 shows the morphological effects of rNetB on LMH cells. Control cells (FIGS. 3A and 3B) demonstrate the epithelial and dendritic-like growth of LMH cells in cell culture. Treatment of cells with purified rNetB ($7.7^{-10}$ mol, 1 h) caused rapid cell blebbing and cell swelling (FIGS. 3C and 3D). Longer incubation periods lead to total cell lysis (data not shown).

Figure 4:
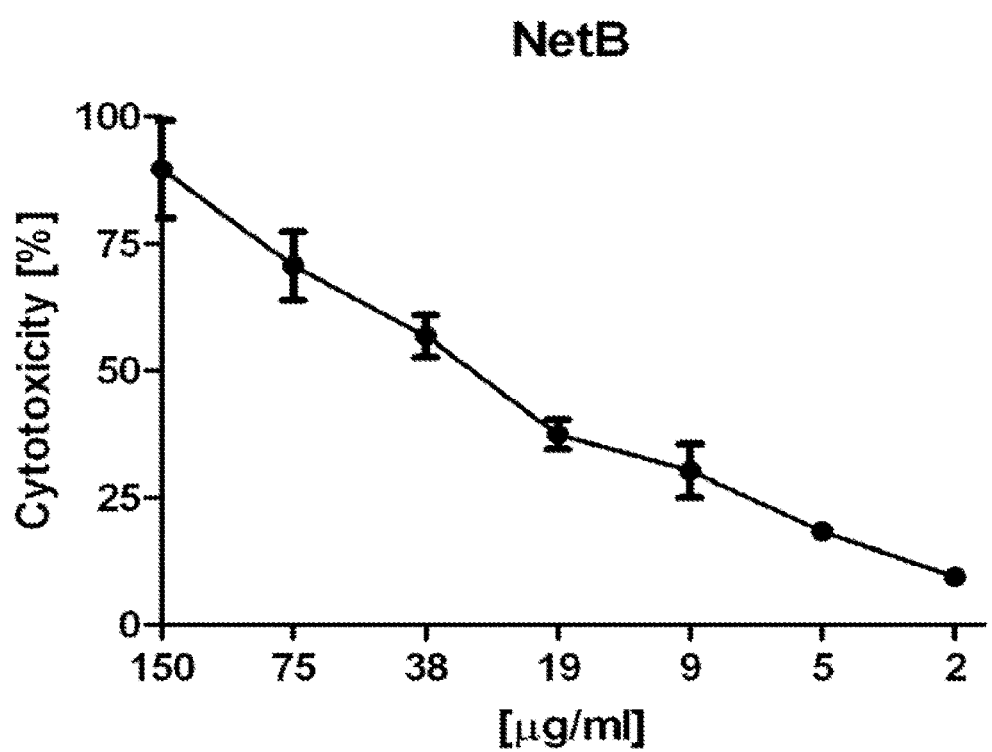
FIG. 4 shows the cytotoxic effect of different concentrations of rNetB on LMH cells.

Consequently, cells were incubated with serial dilutions of NetB in Waymouth's medium (100 μl final volume in each well) for 2 h at 37° C. Control cells were incubated with Waymouth's medium to determine either the base line (0%) or total cell lysis (100%), achieved by freezing and thawing of the cells. After 2 h of incubation the supernatant was assayed and percentage cytotoxicity was determined relative to the control groups (FIG. 4). Each dilution was assayed in six replicates and in three independent experiments (data are means±standard deviations). The median cytotoxic dose ($CT_{50}$) was determined as 29 μg/ml ($7.7^{-10}$ mol).

Generating Formaldehyde Derived NetB Toxoid as Candidate Vaccine

Figure 5:
FIG. 5 shows an SDS PAGE gel of formaldehyde derived NetB toxoid in lane 2, with lane 1 being marker (molecular mass is indicated in kDa at the site)
Figure 6A:
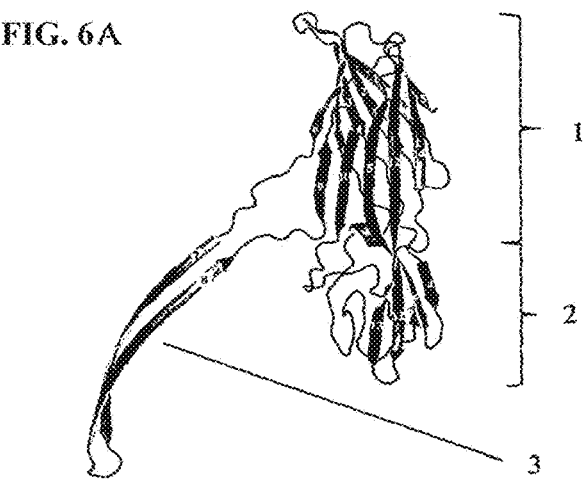
FIGS. 6A, 6B and 6C illustrate the crystal structure of NetB, with FIG. 6A being a ribbon representation of an isolated NetB subunit, FIG. 6B being a close up view of the rim domain 2 and FIG. 6C being a ribbon representation of the NetB assembly viewed from the side.
Figure 6B:
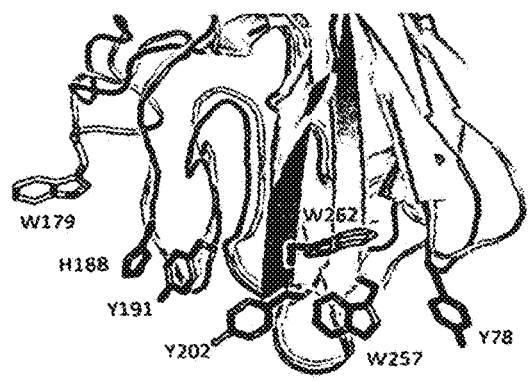
Figure 6C:
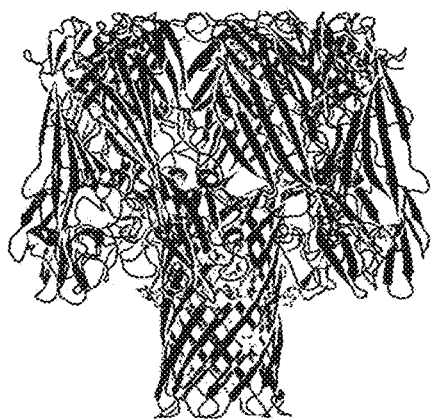

The recombinant NetB was suspended in Tris-buffered saline (TBS) at 400 μg/ml and formaldehyde added to a final concentration of 130 mM. After incubation for 5 days at 37° C., the reaction was stopped by the addition of L-Lysine to 30 mM final concentration and residual formaldehyde was removed by dialysis against TBS buffer. Formaldehyde treatment of the rNetB led to a highly cross-linked protein (FIG. 5). The formaldehyde-derived NetB toxoid was incubated with LMH cells and no cytotoxic effect could be observed (data not shown).

Construction of NetB Mutants

In order to map key residues critical for NetB functionality (cell binding, oligomerisation, pore-formation) a monomeric/heptameric protein model of NetB has been made based on sequence similarities with related pore-forming toxins (data not shown). As a result, the following residues were selected to be replaced by an alanine by site-directed mutagenesis: D81, P138, Y153, G157, Y182, Q184, P185 and R230. The mutants were constructed with the QuikChange II site-directed mutagenesis Kit (Stratagene) by using the primers listed in Table 2 below.

The recombinant pBAD-netB expression vector was then used as a template to amplify the respective mutant netB gene. The rNetB mutants were expressed and purified as described earlier for the rNetB but only two mutants (P185A, R230A) behaved as the wt rNetB in terms of protein stability. The other rNetB mutants (D81A, P138A, Y153A, G157A, Y182A, Q184A) were less soluble and as a consequence were mainly accumulated in inclusion bodies during protein expression. Although in low protein amounts and not very pure, the less stable rNetB mutants could be purified and preliminary data from incubating the rNetB mutants with LMH cells suggest a less-toxic (Y182A) and a non-toxic mutant (P138A).

TABLE 2

Primers used in this study for netB mutagenesis

| Primer | Sequence (5'-3') | SEQ ID NO |
|---|---|---|
| netB_D81A_fwd | GGAACATTTATTGAAGCTCCTCATTCTGATAAGAAAACTGC | 9 |
| netB_D81A_rev | GCAGTTTTCTTATCAGAATGAGGAGCTTCAATAAATGTTCC | 10 |
| netB_P138A_fwd | GCAAATTCTATTGCTAAAAATACTATAGATAAAAAAGATGTATC | 11 |
| netB_P138A_rev | GATACATCTTTTTTATCTATAGTATTTTTAGCAATAGAATTTGC | 12 |
| netB_Y153A_fwd | GATGTATCTAATTCAATTGGTGCGTCTATAGGCGG | 13 |
| netB_Y153A_rev | CCGCCTATAGACGCACCAATTGAATTAGATACATC | 14 |
| netB_G157A_fwd | CAATTGGTTATTCTATAGGCGCTAATATATCTGTTGAAGG | 15 |
| netB_G157A_rev | CCTTCAACAGATATATTAGCGCCTATAGAATAACCAATTG | 16 |
| netB_Y182A_fwd | GTCCAAAATACTATAAGCGCTGAACAACCTGATTTTAGAAC | 17 |
| netB_Y182A_rev | GTTCTAAAATCAGGTTGTTCAGCGCTTATAGTATTTTGGAC | 18 |
| netB_Q184A_fwd | CCAAAATACTATAAGCTATGAAGCACCTGATTTTAGAACAATTC | 19 |
| netB_Q184A_rev | GAATTGTTCTAAAATCAGGTGCTTCATAGCTTATAGTATTTTGG | 20 |
| netB_P185A_fwd | CTATAAGCTATGAACAAGCTGATTTTAGAACAATTCAAAG | 21 |
| netB_P185A_rev | CTTTGAATTGTTCTAAAATCAGCTTGTTCATAGCTTATAG | 22 |
| netB_R230A_fwd | CAATTATTCATGAAATCAGCATTGTATAATAATGGTG | 23 |
| netB_R230A_rev | CACCATTATTATACAATGCTGATTTCATGAATAATTG | 24 |

Expression of rNetB Polypeptides in *Salmonella*

The polynucleotide encoding a NetB polypeptide is expressed in an attenuated *Salmonella* strain such as *Salmonella enterica* serovar *Typhimurium* (e.g., strain SL2361 or χ9241 or χ9352 or AviPro *Salmonella* Vac T), *Salmonella enterica* serovar *Enteriditis* (e.g. AviPro *Salmonella* Vac E), or *Salmonella enterica* serovar *Gallinarum* (e.g. strain JOL916 or Gallivac). A number of different approaches are used. The NetB polynucleotide is cloned into a plasmid (for example, plasmid pSC1901, pSEC10 or pBR322), or inserted onto the chromosome of the *Salmonella* strain (for example into a gene in the shikimate pathway). The expression of the NetB polynucleotide is driven by a constitutive or an inducible promoter (for example the phoP or ompC gene promoter). The protein is exported by fusing it to a component of a system such as ClyA.

Vaccination in a Mouse Model

A recombinant *Salmonella* vaccine is tested in BALB/c mice. Groups of 10 mice are immunised intragastrically using a gavage needle with approximately $10^9$ cfu of recombinant *Salmonella* expressing at least one rNetB mutant as described above, for example, Y182A comprising polypeptide sequence SEQ ID NO:5 or P138A comprising polypeptide sequence SEQ ID NO:6. The cells are re-suspended in 100 μl LB broth. Mice are immunised on days 0, 14, 28, 42 and 56. Tail vein serum samples are collected on days 13, 27, 41, 55, 69 and 83 and the concentration of any antibody against NetB present determined using an ELISA.

Vaccination in a Chicken Model

Figure 7A:
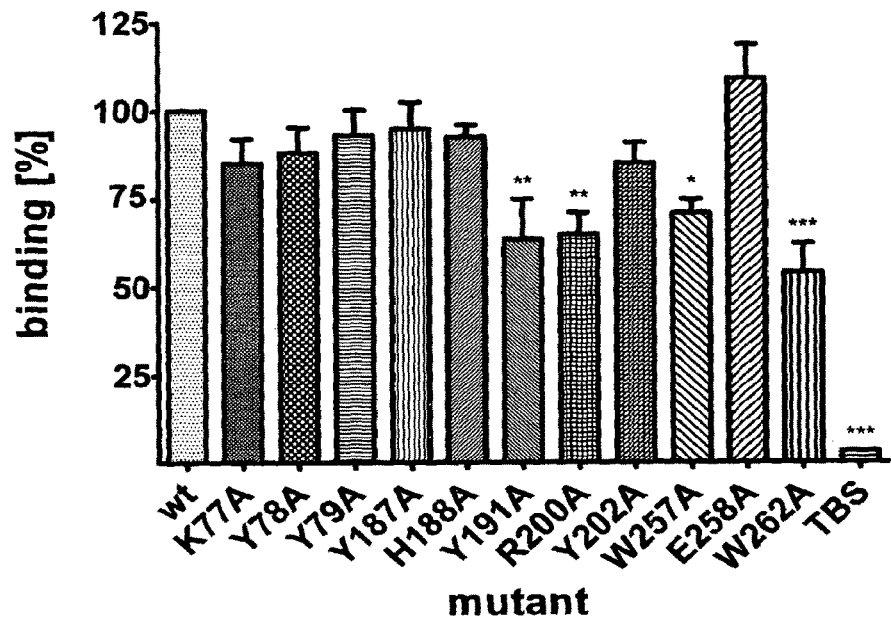
FIGS. 7A to 7D illustrate a functional analysis of various NetB rim mutants.
Figure 7B:
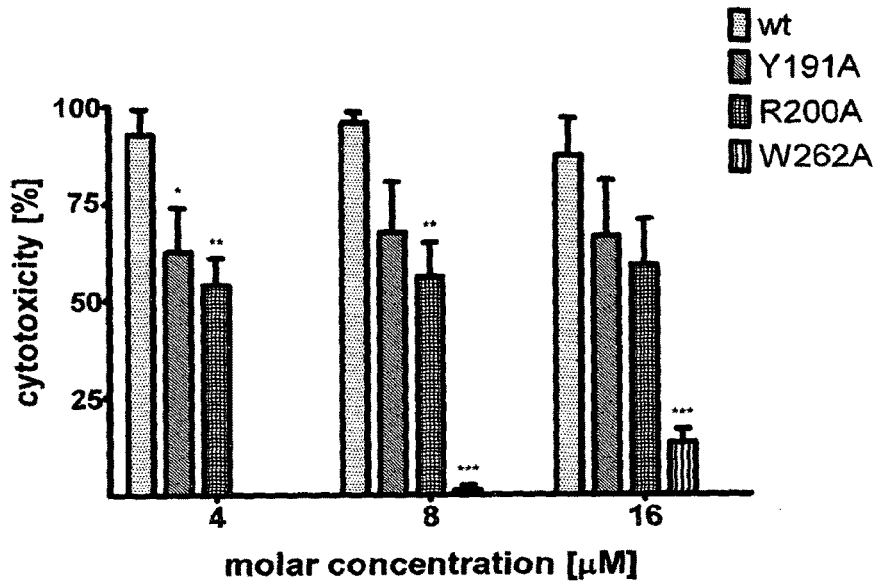
Figure 7C:
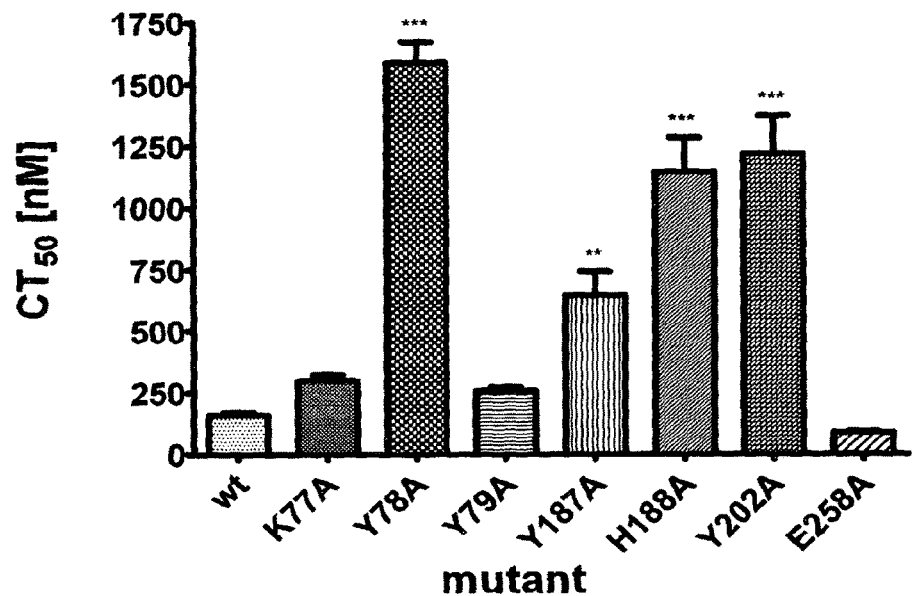
Figure 7D:
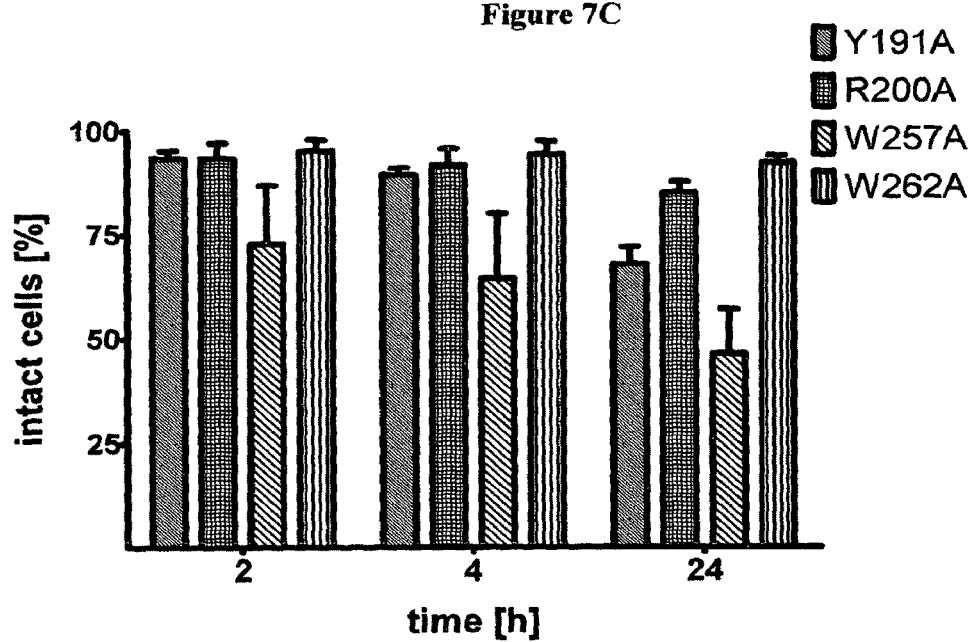
Figure 8:
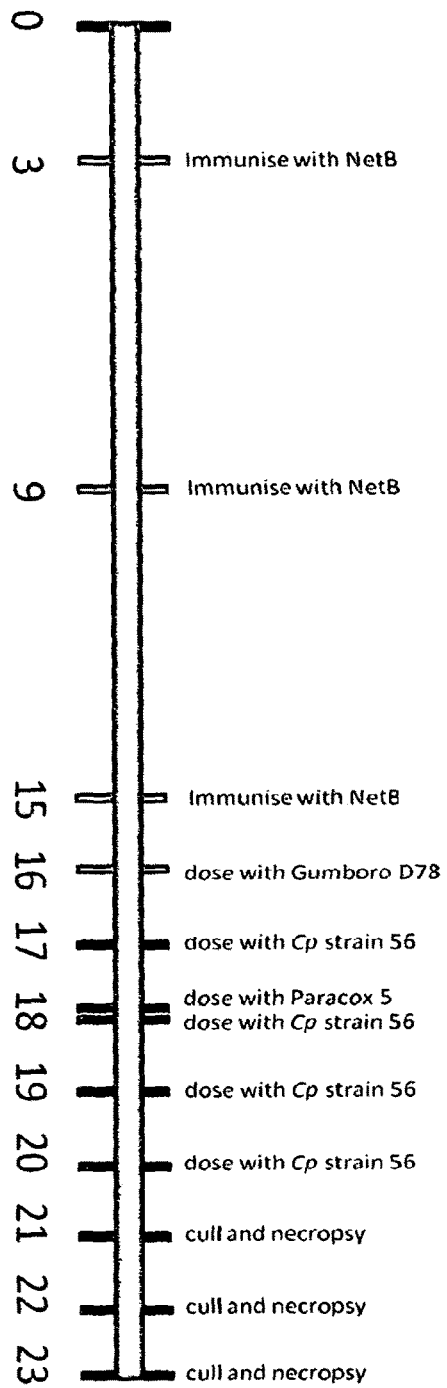
FIG. 8 shows a necrotic enteritis model for studying immunisation of broiler chickens with antigen over time.
Figure 11:
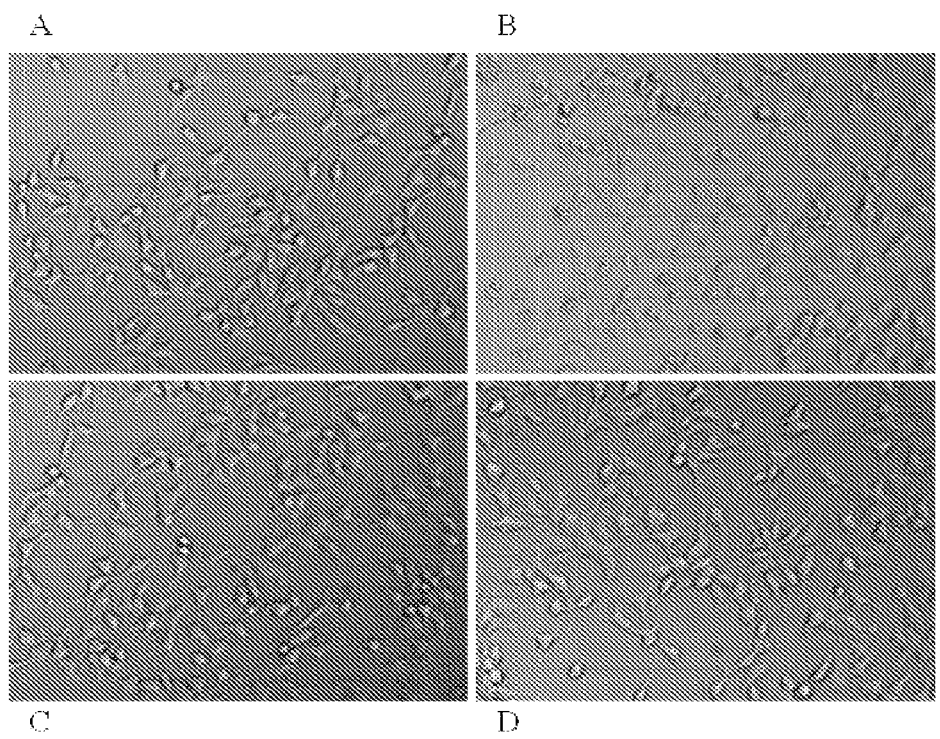
FIG. 11 shows the cytotoxic effect of wild type NetB (panel B), formaldehyde NetB toxoid (panel C) and NetB W262A (panel D) on LMH cells (panel A shows untreated cells)

20 μg of toxoid is administered with QuilA adjuvant (1:1) to each bird. Three doses are given at one week intervals, intramuscularly in the breast muscle. Animals are bled at 1 week after the last immunisation and challenge and the concentration of any antibody against NetB present determined using an ELISA. For mass dosing the vaccine is administered via drinking water, foodstuffs or as a spray.

Crystallisation and Data Processing.

The NetB gene (GenBank accession number: A8ULG6) was cloned, overexpressed in *E. coli* and purified in monomeric form using Ni-NTA chromatography. NetB oligomer was obtained by incubating monomeric NetB with cholesterol rich liposomes and subsequently solubilised using detergent.

NetB oligomer was crystallised initially using the sitting drop method in 12% (w/v) PEG 4000, 100 mM sodium cacodylate pH 6.5. However, these crystals were too small for diffraction studies. Optimisation using a combination of limited trypsin proteolysis and the addition of the additive detergent polyethylene glycol dodecyl ether (THESIT® part of the Hampton detergent screen) led to crystals which diffracted to ~4 Å. Data were collected on a Rigaku Saturn 944 CCD detector mounted onto a Rigaku Micromax X-ray generator. Data were indexed and integrated with Mosflm (Battye T G G et al (2011) *Acta Crystallographica Section D* vol 67(4): 271-281), and scaled using SCALA (Evans P. (2006) *Acta Crystallogr D Biol Crystallogr.* 62 (Pt 1): 72-82). Molecular replacement was carried out using Phaser MR (McCoy et al. (2007) *J Applied Crystallogr.* 40 (Pt 4): 658-674) and the αHL heptamer structure (PDB ID 7AHL) as a search model. The initial model refined using Phenix (Adams P D et al. (2010) *Acta Crystallogr D Biol Crystallogr.* 66 (Pt 2): 213-221) with NCS, Ramachandran and secondary structure restraints, and increased weighting on stereochemical terms. At the final stages, refinement was carried out using Buster (Smart O S, et al. (2012) *Acta Crystallogr D Biol Crystallogr.* 68 (Pt 4): 368-380) with NCS and reference structure restraints (αHL used as a closely related reference structure). Manual building and real space refinement was performed using COOT (Elmsley P et al, (2010) *Acta Crystallogr D Biol Crystallogr.* 66 (Pt 4): 486-501), and model validation was calculated using Molprobity (Davis et al. (2007) *Nucleic Acids Res* 35: W375-383). The PYMOL™ Molecular Graphics System was used for visualisation and electrostatic potential surface rendering. A model with all side-chains present was used for electrostatic potential calculation even when side-chain density was not visible in the electron density map.

The crystal structure of NetB is illustrated in FIGS. 6A to 6C of the accompanying drawings. FIG. 6A is a ribbon representation of an isolated NetB subunit. As with αHL, there are three domains; a β-sandwich domain 1, a rim domain 2 and a stem domain 3. FIG. 6B is a close up view of the rim domain 2. Residues in NetB that were further investigated by mutation to evaluate their function are shown in stick representation. FIG. 6C illustrates the NetB assembly viewed from the side.

Each NetB monomer contains 15 β-strands accounting for 53% of the polypeptide, whilst the remainder is made up of one $3_{10}$-helix, one short α-helix and random coil. The β-sandwich domain consists of two β-sheets composed of strands 1, 2, 3, 6, 11 and 5, 9, 10, 12, 14, 15, respectively, and a single α-helix. Strands 5 and 12 extend into the lower part of the molecule, and these strands, along with strands 4 and 13, the $3_{10}$-helix and considerable random coil, make up the rim domain. The stem domain contains the long, curved amphipathic hairpin (strands 7 and 8), which is connected to the β-sandwich domain through two short coils, forming a triangle region similar to that in other membrane-inserted βPFTs. Superposition with the *S. aureus* αHL monomer results in an rmsd of 1.55 Å. With the exception of two small β-strands which are absent in NetB (αHL strands 11 and 12), secondary structure elements are largely conserved between the two toxins. Areas of small structural deviation to αHL exist in all three domains. For example, loop positions in the β-sandwich domain between strands 5 and 6 and strands 11 and 12 deviate from the corresponding loops in αHL. Strand 15 in αHL, which spans the rim and β-sandwich domains, is composed of two separate strands (13 and 14) in NetB. Finally, while the NetB stem domain adopts a similar curvature to αHL, the turn at the cytoplasmic end bends inwards towards the pore lumen in NetB. The most interesting differences between the two toxins lie in the area that constitutes the rim loops.

The rim domain is thought to be the region that interacts with the target cell membrane. Therefore, further studies were carried out to determine whether mutation of key residues along the rim loops, affect NetB function. Mutants showing a significant difference relative to wild type NetB are summarised in Table 3 below.

FIGS. 7A to 7D show binding ability of various mutants to LMH cells relative to wild type NetB. LMH cytotoxicity was performed as outlined hereinafter. Mutants Y191A, R200A, W257A and W262A showed significantly reduced binding compared to wild type toxin, see FIG. 7A. Subsequently, the three NetB mutants showing the lowest affinity in an in situ Western (i.e., ON-CELL WESTERN™) assay (Y191A, R200A, and W262) were tested for their abilities to cause lysis of LMH cells at 4, 8, or 16 μM concentrations (FIG. 7B). All 3 mutants showed reduced cytotoxicity relative to wild type NetB, with W262A showing the highest decrease.

TABLE 3

Functional characteristics of NetB mutants. (Asterisks indicate a statistically significant difference relative to wild type NetB (*: $p < 0.001$; : $p < 0.01$; *: $p < 0.05$; 1-way ANOVA). N.D.: not determined).

| NetB mutant | Reduced binding on LMH cells | Reduced haemolysis on RBCs | Reduced cytotoxicity on LMH cells |
|---|---|---|---|
| Y78A | / | *** | N.D. |
| Y187A | / | ** | N.D. |
| H188A | / | *** | N.D. |
| Y191A | ** | *** | * |
| R200A | ** | *** | ** |
| Y202A | / | *** | N.D. |
| W257A | * | *** | N.D. |
| W262A | *** | *** | *** |

In addition, the hemolytic activity of NetB was evaluated by incubating the toxin with human red blood cells (hRBCs). hRBC hemolysis was performed using standard procedure known in the art. FIG. 7C shows the $CT_{50}$ values of the NetB variants. However, $CT_{50}$ values of mutants Y191A, R200A, W257A, and W262A could not be determined as they only caused incomplete hemolysis within 1 h, even at 5 μM concentrations. Therefore, these mutants were incubated with hRBCs for an extended period and degree of hemolysis was monitored at 2, 4, and 24 h (FIG. 7D). Again, mutants Y191A, R200A, W257A and W262 showed the most significant decrease in activity relative to wild type NetB. In addition, mutants Y78A, Y187A, H188A and Y202A also showed a significant increase in $CT_{50}$ values.

In summary, replacement of conserved residues along the rim loops of NetB (Y191, R200, W257, and W262) had the most dramatic effect on NetB cell binding and toxicity. In addition, due to the broader dynamic range of the hemolysis assay, it could be shown that non-conserved residues such as Y78, Y187, H188, and Y202 also play a role in NetB function.

The position of the mutations referred to in Table 3 above is numbered as found in SEQ ID NO:1 and thus the position of the mutation in the full-length protein will be plus 30 amino acids. Accordingly, Y191A is Y221A (SEQ ID NO:36), R200A is R230A (SEQ ID NO: 37), W257A is W287A (SEQ ID NO: 38) and W262A is W292A (SEQ ID NO: 39). The NetB mutant W262A (W292A in SEQ ID NO:3) was shown to cause the most significant reduction in toxicity so it was decided to test NetB W262A (SEQ ID NO: 39) or a formaldehyde NetB toxoid for their potential to protect chickens against NE in an in vivo model.

The expression and purification of NetB in *E. coli* was carried out as hereinbefore described using the bacterial strains and plasmids listed in Table 1. The preparation of a formaldehyde NetB toxoid was also carried out as outlined above.

Expression and Purification of NetB W262A(W292A) in *E. coli.*

Bacterial cells were grown in TB at 37° C. and expression of NetB induced by the addition of arabinose. The cells were lysed using BugBuster and NetB purified using a His-tag column at a concentration of 1.7 mg/ml.

The purified proteins were analysed by SDS-PAGE as previously described and the results are shown in FIGS. 9 and 10.

Cytotoxicity Towards LMH Cells.

The NetB was evaluated for its cytotoxicity to a chicken hepatocellular carcinoma epithelial cell line (LMH; ATTC: CRL-2117). Therefore, LMH cells were grown in Waymouth's MB 752/1 medium (Invitrogen) supplemented with 10% fetal calf serum at 37° C. in a 5% $CO_2$ incubator to 70-80% confluency on 96-well plates. Subsequently, cells were incubated with 0.4 mg/ml of wild type NetB, formaldehyde NetB toxoid, or NetB W262A. Effects on cell morphology were observed with an optical microscope, as shown in FIG. 11. Untreated cells had epithelial and dendritic-like growth (panel A). Treatment of the cells with purified NetB caused rapid cell blebbing and swelling (panel B). In contrast, incubation with a formaldehyde NetB toxoid or NetB W262A did not result in morphological changes indicative of toxicity to LMH cells (panels C and D).

Immunisation with Formaldehyde NetB Toxoid and NetB W262A.

A formaldehyde NetB toxoid and NetB W262A were used in an in vivo model. Ross 308 broiler chickens were obtained as one-day-old chicks from a local commercial hatchery. All treatment groups were housed in the same room. The birds were reared in pens at a density of 25 animals per 1 $m^2$ on wood shavings. All pens were separated by solid walls to prevent contact between birds from different treatment groups. Before the trial, the rooms were decontaminated with Metatectyl HQ (CLIM'MEDIC®, Metatecta, Belgium) and a commercial anticoccidial desinfectant (OOCIDE, DuPont Animal Health Solutions, Wilmington, US). The chickens were divided in 4 groups of 25 animals. They received ad libitum drinking water and feed. A 23 h/1 h light/darkness program was applied. The animal experiments were carried out according to the recommendations and following approval of the Ethical Committee of the Faculty of Veterinary Medicine, Ghent University.

The NE model was based on the subclinical in vivo model described previously in Gholamiandehkordi et al (2007) *Avian Pathol* October; 36(5): 375-82. Groups of 25 one-day-old Ross 308 broiler chickens were fed a wheat/rye-based (43%/7.5%) diet, with soybean meal as protein source. The feed composition is described in Gholamiandehkordi et al (supra). Nobilis Gumboro D 78 vaccine (Schering-Plough Animal Health, Brussels, Belgium) was given in the drinking water on day 16 in all groups. From day 17 onwards soy bean meal was replaced by fishmeal (30%) as protein source. All groups were orally challenged once a day on day 17, 18, 19 and 20 with approximately $4\times10^8$ cfu *C. perfringens* strain 56 bacteria. On day 18 all groups were orally inoculated with a ten-fold dose of Paracox-5 (Schering-Plough Animal Health, Brussels, Belgium). On day 21, 22, 23, each time one-third of the birds was euthanized and necropsied, as schematically shown in FIG. 8.

Lesions in the small intestine (duodenum to ileum) were scored (as described by Keyburn et al. (2006) *Infect Immun* vol 74: 6496-6500) as follows: 0=no gross lesions; 1=congested intestinal mucosa; 2=small focal necrosis or ulceration (1-5 foci); 3=focal necrosis or ulceration (6-15 foci); 4=focal necrosis or ulceration (16 or more foci); 5=patches of necrosis 2-3 cm long; 6=diffuse necrosis typical of field cases. Lesion scores of 2 or more were classified as NE positive. As controls, animals were unimmunized or treated only with adjuvant.

As demonstrated in FIG. 12, both antigens significantly reduced lesion scores relative to the control groups. No difference could be detected between the non-vaccinated and the adjuvant-only controls. This clearly shows that a formaldehyde NetB toxoid or NetB W262A could also form the basis of an effective vaccine for NE. Although both antigens significantly increased protection, the usage of a recombinant protein brings the added advantage of not having to test every batch of a formaldehyde NetB toxoid for safety.

DISCUSSION

In this study, an expression system for netB in *E. coli* has been established and it has been shown that the recombinant protein is able to form oligomeric complexes. Cytotoxicity assays on LMH cells, a cell line approved to be susceptible for NetB (Keybum et al., (2008) *PLoS Pathog* vol 4: e26), showed that the recombinant toxin is capable of forming functional pores and causing cell lysis. Based on sequence similarities with related pore-forming toxins, a monomeric/heptameric model of NetB has been designed (data not shown) and used to identify amino acids that, if replaced by another, could have a dramatic impairment on NetB functionality, e.g. cell binding, oligomerisation, or pore-formation. Consequently, eight NetB mutants were designed by site directed mutagenesis (D81A, P138A, Y153A, G157A, Y182A, Q184A, P185A, R230A).

Surprisingly, preliminary incubation of these rNetB mutants on LMH cells indicate that only two of the mutants had reduced toxicity, with one less-toxic Y182A and one non-toxic (P138A) mutant (compared to wild type rNetB).

The tyrosine at position 182 is located within the cap region and might be crucial maintaining the correct orientation of the stem and the cap, as well as for interacting with the membrane-lipids during pore-formation. The proline at position 138 is thought to play a crucial role in the pore-formation process, as it is located at the end of the beta-hairpin structure. During pore-formation, the unfolding of the beta-hairpin into the membrane is an essential step in building up the functional beta-barrel pore complex.

This study has used a formaldehyde-derived toxoid or a non-toxic variant of the NetB to immunise chicken and thereby stimulating a specific antibody response to protect chicken from a subsequent toxin challenge.

As described herein, further studies were then carried out to investigate the crystal structure of the heptameric complex of NetB in detergent. The heptameric structure, which is likely to represent the membrane-inserted pore-form, was found to have high structural similarity to the Staphylococcal toxin α-HL, revealing conservation of many of the key residues that are important for function in this family of β-PFTs but displaying differences that may have evolved separately in the Clostridial counterparts. Residues critical for NetB binding and toxicity were also identified.

As described above, replacement of conserved residues along the rim loops of NetB (Y191, R200, W257, and W262) had the most dramatic effect on NetB cell binding and toxicity. In addition, due to the broader dynamic range of the hemolysis assay, it could be shown that non-conserved residues such as Y78, Y187, H188, and Y202 also play a role in NetB function.

Thus it can be seen that mutation of residues contained within the rim domain, particularly those highly conserved in β-PFTs of *S. aureus* and *C. perfringens* or within a pore-forming domain, such as the β-hairpin structure can significantly affect host-cell binding and consequently, cytotoxicity of NetB. Such recombinant proteins have real potential for use as an effective vaccine against NE.

The invention claimed is:

1. A polynucleotide having a nucleic acid sequence which encodes for a polypeptide having at least 60% sequence identity to SEQ ID NO:1 and comprising the amino acid sequence ETTQXRGTNK (SEQ ID NO:46) where "X" is any amino acid other than W, the polypeptide being capable of binding an antibody which binds to SEQ ID NO:1 and having reduced toxicity compared with the toxicity of SEQ ID NO:1.

2. A polynucleotide according to claim 1 where "X" is A.

3. A polynucleotide according to claim 1 comprising any one selected from the group consisting of SEQ ID NOs: 31, 32, 48, 49, 50 and 51.

4. A vector comprising the polynucleotide according to claim 1.

5. A vector comprising the polynucleotide according to claim 2.

6. A vector comprising the polynucleotide according to claim 3.

7. A vector according to claim 4 wherein the vector is a plasmid or a virus.

8. A vector according to claim 5 wherein the vector is a plasmid or a virus.

9. A vector according to claim 6 wherein the vector is a plasmid or a virus.

10. A vector according to claim 4 wherein the vector is a eukaryotic virus vector.

11. A vector according to claim 5 wherein the vector is a eukaryotic virus vector.

12. A vector according to claim 6 wherein the vector is a eukaryotic virus vector.

13. A vector according to claim 4 wherein the vector is vaccinia virus.

14. A vector according to claim 5 wherein the vector is vaccinia virus.

15. A vector according to claim 6 wherein the vector is vaccinia virus.

16. A cell comprising the polynucleotide according to claim 1.

17. A cell comprising the polynucleotide according to claim 2.

18. A cell comprising the polynucleotide according to claim 3.

19. A cell according to claim 16 which is a bacterial cell.

20. A cell according to claim 19 which is a *Salmonella* cell.

* * * * *

SEQUENCE LISTING

<160> NUMBER OF SEQ ID NOS: 51

<210> SEQ ID NO 1
<211> LENGTH: 292
<212> TYPE: PRT
<213> ORGANISM: Clostridium perfringens

<400> SEQUENCE: 1

Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
        115                 120                 125

Ile Ser Val Glu Gly Lys Thr Ala Gly Ala Gly Ile Asn Ala Ser Tyr
    130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
            180                 185                 190

Asn Gln Leu Phe Met Lys Ser Arg Leu Tyr Asn Asn Gly Asp Lys Asn
        195                 200                 205

Phe Thr Asp Asp Arg Asp Leu Ser Thr Leu Ile Ser Gly Gly Phe Ser
    210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn

```
                    245                 250                 255

Trp Glu Thr Thr Gln Trp Arg Gly Thr Asn Lys Leu Ser Ser Thr Ser
            260                 265                 270

Glu Tyr Asn Glu Phe Met Phe Lys Ile Asn Trp Gln Asp His Lys Ile
        275                 280                 285

Glu Tyr Tyr Leu
        290

<210> SEQ ID NO 2
<211> LENGTH: 331
<212> TYPE: PRT
<213> ORGANISM: Artificial Sequence
<220> FEATURE:
<223> OTHER INFORMATION: Expression construct

<400> SEQUENCE: 2

Met Gly Gly Ser His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Leu Glu Ser Glu Leu Asn Asp Ile Asn Lys Ile
        35                  40                  45

Glu Leu Lys Asn Leu Ser Gly Glu Ile Ile Lys Glu Asn Gly Lys Glu
    50                  55                  60

Ala Ile Lys Tyr Thr Ser Ser Asp Thr Ala Ser His Lys Gly Trp Lys
65                  70                  75                  80

Ala Thr Leu Ser Gly Thr Phe Ile Glu Asp Pro His Ser Asp Lys Lys
                85                  90                  95

Thr Ala Leu Leu Asn Leu Glu Gly Phe Ile Pro Ser Asp Lys Gln Ile
            100                 105                 110

Phe Gly Ser Lys Tyr Tyr Gly Lys Met Lys Trp Pro Glu Thr Tyr Arg
        115                 120                 125

Ile Asn Val Lys Ser Ala Asp Val Asn Asn Ile Lys Ile Ala Asn
        130                 135                 140

Ser Ile Pro Lys Asn Thr Ile Asp Lys Lys Asp Val Ser Asn Ser Ile
145                 150                 155                 160

Gly Tyr Ser Ile Gly Gly Asn Ile Ser Val Glu Gly Lys Thr Ala Gly
                165                 170                 175

Ala Gly Ile Asn Ala Ser Tyr Asn Val Gln Asn Thr Ile Ser Tyr Glu
            180                 185                 190

Gln Pro Asp Phe Arg Thr Ile Gln Arg Lys Asp Asp Ala Asn Leu Ala
        195                 200                 205

Ser Trp Asp Ile Lys Phe Val Glu Thr Lys Asp Gly Tyr Asn Ile Asp
    210                 215                 220

Ser Tyr His Ala Ile Tyr Gly Asn Gln Leu Phe Met Lys Ser Arg Leu
225                 230                 235                 240

Tyr Asn Asn Gly Asp Lys Asn Phe Thr Asp Asp Arg Asp Leu Ser Thr
                245                 250                 255

Leu Ile Ser Gly Gly Phe Ser Pro Asn Met Ala Leu Ala Leu Thr Ala
            260                 265                 270

Pro Lys Asn Ala Lys Glu Ser Val Ile Val Glu Tyr Gln Arg Phe
        275                 280                 285

Asp Asn Asp Tyr Ile Leu Asn Trp Glu Thr Thr Gln Trp Arg Gly Thr
    290                 295                 300

Asn Lys Leu Ser Ser Thr Ser Glu Tyr Asn Glu Phe Met Phe Lys Ile
```

```
305                 310                 315                 320

Asn Trp Gln Asp His Lys Ile Glu Tyr Tyr Leu
                325                 330

<210> SEQ ID NO 3
<211> LENGTH: 322
<212> TYPE: PRT
<213> ORGANISM: Clostridium perfringens

<400> SEQUENCE: 3

Met Lys Arg Leu Lys Ile Ile Ser Ile Thr Leu Val Leu Thr Ser Val
1               5                   10                  15

Ile Ser Thr Ser Leu Phe Ser Thr Gln Thr Gln Val Phe Ala Ser Glu
            20                  25                  30

Leu Asn Asp Ile Asn Lys Ile Glu Leu Lys Asn Leu Ser Gly Glu Ile
        35                  40                  45

Ile Lys Glu Asn Gly Lys Glu Ala Ile Lys Tyr Thr Ser Ser Asp Thr
    50                  55                  60

Ala Ser His Lys Gly Trp Lys Ala Thr Leu Ser Gly Thr Phe Ile Glu
65                  70                  75                  80

Asp Pro His Ser Asp Lys Lys Thr Ala Leu Leu Asn Leu Glu Gly Phe
                85                  90                  95

Ile Pro Ser Asp Lys Gln Ile Phe Gly Ser Lys Tyr Tyr Gly Lys Met
            100                 105                 110

Lys Trp Pro Glu Thr Tyr Arg Ile Asn Val Lys Ser Ala Asp Val Asn
        115                 120                 125

Asn Asn Ile Lys Ile Ala Asn Ser Ile Pro Lys Asn Thr Ile Asp Lys
    130                 135                 140

Lys Asp Val Ser Asn Ser Ile Gly Tyr Ser Ile Gly Gly Asn Ile Ser
145                 150                 155                 160

Val Glu Gly Lys Thr Ala Gly Ala Gly Ile Asn Ala Ser Tyr Asn Val
                165                 170                 175

Gln Asn Thr Ile Ser Tyr Glu Gln Pro Asp Phe Arg Thr Ile Gln Arg
            180                 185                 190

Lys Asp Asp Ala Asn Leu Ala Ser Trp Asp Ile Lys Phe Val Glu Thr
        195                 200                 205

Lys Asp Gly Tyr Asn Ile Asp Ser Tyr His Ala Ile Tyr Gly Asn Gln
    210                 215                 220

Leu Phe Met Lys Ser Arg Leu Tyr Asn Asn Gly Asp Lys Asn Phe Thr
225                 230                 235                 240

Asp Asp Arg Asp Leu Ser Thr Leu Ile Ser Gly Gly Phe Ser Pro Asn
                245                 250                 255

Met Ala Leu Ala Leu Thr Ala Pro Lys Asn Ala Lys Glu Ser Val Ile
            260                 265                 270

Ile Val Glu Tyr Gln Arg Phe Asp Asn Asp Tyr Ile Leu Asn Trp Glu
        275                 280                 285

Thr Thr Gln Trp Arg Gly Thr Asn Lys Leu Ser Ser Thr Ser Glu Tyr
    290                 295                 300

Asn Glu Phe Met Phe Lys Ile Asn Trp Gln Asp His Lys Ile Glu Tyr
305                 310                 315                 320

Tyr Leu

<210> SEQ ID NO 4
<211> LENGTH: 969
<212> TYPE: DNA
```

<213> ORGANISM: Clostridium perfringens

<400> SEQUENCE: 4

```
atgaaaagat taaaaattat ttcaattaca ctagttctta caagtgtaat tagtacaagc      60
cttttttcaa ctcaaactca agtttttgca agtgaattaa atgacataaa caaaattgag     120
ttgaaaaatc taagtggaga ataataaaaa gaaatggaa aggaagctat aaatatact      180
tctagtgata ccgcttcaca taaaggttgg aaggcaactt aagtggaac atttattgaa     240
gatcctcatt ctgataagaa aactgcttta ttaaatttag aaggatttat accttctgat     300
aaacagattt ttggttctaa atattacgga aaaatgaaat ggcctgaaac ttatagaatt     360
aatgtaaaaa gtgctgatgt aaataataat ataaaaatag caaattctat tcctaaaaat     420
actatagata aaaagatgt atctaattca attggttatt ctataggcgg taatatatct     480
gttgaaggaa aaactgctgg tgctggaata aatgcttcat ataatgtcca aaatactata     540
agctatgaac aacctgattt tagaacaatt caaagaaaag atgatgcaaa cttagcatca     600
tgggatataa aatttgttga gactaaggac ggttataata tagattctta tcatgctatt     660
tatggaaatc aattattcat gaaatcaaga ttgtataata atggtgataa aaatttcaca     720
gatgatagag atttatcaac attaatttct ggtggatttt cacccaatat ggctttagca     780
ttaacagcac taaaaatgc taaagaatct gtaataatag ttgaatatca aagatttgat     840
aatgactata ttttaaattg ggaaactact caatggcgag aacaaacaa actttcgtca     900
acaagtgaat ataacgaatt tatgtttaaa ataaattggc aagatcataa aatagaatat     960
tatctgtaa                                                             969
```

<210> SEQ ID NO 5
<211> LENGTH: 292
<212> TYPE: PRT
<213> ORGANISM: Artificial Sequence
<220> FEATURE:
<223> OTHER INFORMATION: Mutated sequence

<400> SEQUENCE: 5

```
Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
        115                 120                 125

Ile Ser Val Glu Gly Lys Thr Ala Gly Ala Gly Ile Asn Ala Ser Tyr
    130                 135                 140

Asn Val Gln Asn Thr Ile Ser Ala Glu Gln Pro Asp Phe Arg Thr Ile
145                 150                 155                 160

Gln Arg Lys Asp Asp Ala Asn Leu Ala Ser Trp Asp Ile Lys Phe Val
```

```
                      165                 170                 175

Glu Thr Lys Asp Gly Tyr Asn Ile Asp Ser Tyr His Ala Ile Tyr Gly
                180                 185                 190

Asn Gln Leu Phe Met Lys Ser Arg Leu Tyr Asn Asn Gly Asp Lys Asn
            195                 200                 205

Phe Thr Asp Asp Arg Asp Leu Ser Thr Leu Ile Ser Gly Gly Phe Ser
        210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
                245                 250                 255

Trp Glu Thr Thr Gln Trp Arg Gly Thr Asn Lys Leu Ser Ser Thr Ser
            260                 265                 270

Glu Tyr Asn Glu Phe Met Phe Lys Ile Asn Trp Gln Asp His Lys Ile
        275                 280                 285

Glu Tyr Tyr Leu
        290

<210> SEQ ID NO 6
<211> LENGTH: 292
<212> TYPE: PRT
<213> ORGANISM: Artificial Sequence
<220> FEATURE:
<223> OTHER INFORMATION: Mutated sequence

<400> SEQUENCE: 6

Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
                20                  25                  30

Asp Thr Ala Ser His Lys Gly Trp Lys Ala Thr Leu Ser Gly Thr Phe
            35                  40                  45

Ile Glu Asp Pro His Ser Asp Lys Lys Thr Ala Leu Leu Asn Leu Glu
        50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Asn Ile Lys Ile Ala Asn Ser Ile Ala Lys Asn Thr Ile
                100                 105                 110

Asp Lys Lys Asp Val Ser Asn Ser Ile Gly Tyr Ser Ile Gly Gly Asn
            115                 120                 125

Ile Ser Val Glu Gly Lys Thr Ala Gly Ala Gly Ile Asn Ala Ser Tyr
        130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
                180                 185                 190

Asn Gln Leu Phe Met Lys Ser Arg Leu Tyr Asn Asn Gly Asp Lys Asn
            195                 200                 205

Phe Thr Asp Asp Arg Asp Leu Ser Thr Leu Ile Ser Gly Gly Phe Ser
        210                 215                 220

Pro Asn Met Ala Leu Ala Leu Thr Ala Pro Lys Asn Ala Lys Glu Ser
```

```
            225                 230                 235                 240

Val Ile Ile Val Glu Tyr Gln Arg Phe Asp Asn Asp Tyr Ile Leu Asn
                    245                 250                 255

Trp Glu Thr Thr Gln Trp Arg Gly Thr Asn Lys Leu Ser Ser Thr Ser
                260                 265                 270

Glu Tyr Asn Glu Phe Met Phe Lys Ile Asn Trp Gln Asp His Lys Ile
            275                 280                 285

Glu Tyr Tyr Leu
        290

<210> SEQ ID NO 7
<211> LENGTH: 33
<212> TYPE: DNA
<213> ORGANISM: Artificial Sequence
<220> FEATURE:
<223> OTHER INFORMATION: Primer sequence

<400> SEQUENCE: 7
cccgggctcg agagtgaatt aaatgacata aac                                 33

<210> SEQ ID NO 8
<211> LENGTH: 36
<212> TYPE: DNA
<213> ORGANISM: Artificial Sequence
<220> FEATURE:
<223> OTHER INFORMATION: Primer sequence

<400> SEQUENCE: 8
cccgggaagc ttttacagat aatattctat tttatg                              36

<210> SEQ ID NO 9
<211> LENGTH: 41
<212> TYPE: DNA
<213> ORGANISM: Artificial Sequence
<220> FEATURE:
<223> OTHER INFORMATION: Primer sequence

<400> SEQUENCE: 9
ggaacattta ttgaagctcc tcattctgat aagaaaactg c                        41

<210> SEQ ID NO 10
<211> LENGTH: 41
<212> TYPE: DNA
<213> ORGANISM: Artificial Sequence
<220> FEATURE:
<223> OTHER INFORMATION: Primer sequence

<400> SEQUENCE: 10
gcagttttct tatcagaatg aggagcttca ataaatgttc c                        41

<210> SEQ ID NO 11
<211> LENGTH: 44
<212> TYPE: DNA
<213> ORGANISM: Artificial Sequence
<220> FEATURE:
<223> OTHER INFORMATION: Primer sequence

<400> SEQUENCE: 11
gcaaattcta ttgctaaaaa tactatagat aaaaagatg tatc                      44

<210> SEQ ID NO 12
<211> LENGTH: 44
<212> TYPE: DNA
<213> ORGANISM: Artificial Sequence
```

<220> FEATURE:
<223> OTHER INFORMATION: Primer sequence

<400> SEQUENCE: 12
gatacatctt ttttatctat agtatttta gcaatagaat ttgc        44

<210> SEQ ID NO 13
<211> LENGTH: 35
<212> TYPE: DNA
<213> ORGANISM: Artificial Sequence
<220> FEATURE:
<223> OTHER INFORMATION: Primer sequence

<400> SEQUENCE: 13
gatgtatcta attcaattgg tgcgtctata ggcgg        35

<210> SEQ ID NO 14
<211> LENGTH: 35
<212> TYPE: DNA
<213> ORGANISM: Artificial Sequence
<220> FEATURE:
<223> OTHER INFORMATION: Primer sequence

<400> SEQUENCE: 14
ccgcctatag acgcaccaat tgaattagat acatc        35

<210> SEQ ID NO 15
<211> LENGTH: 40
<212> TYPE: DNA
<213> ORGANISM: Artificial Sequence
<220> FEATURE:
<223> OTHER INFORMATION: Primer sequence

<400> SEQUENCE: 15
caattggtta ttctataggc gctaatatat ctgttgaagg        40

<210> SEQ ID NO 16
<211> LENGTH: 40
<212> TYPE: DNA
<213> ORGANISM: Artificial Sequence
<220> FEATURE:
<223> OTHER INFORMATION: Primer sequence

<400> SEQUENCE: 16
ccttcaacag atatattagc gcctatagaa taaccaattg        40

<210> SEQ ID NO 17
<211> LENGTH: 41
<212> TYPE: DNA
<213> ORGANISM: Artificial Sequence
<220> FEATURE:
<223> OTHER INFORMATION: Primer sequence

<400> SEQUENCE: 17
gtccaaaata ctataagcgc tgaacaacct gattttagaa c        41

<210> SEQ ID NO 18
<211> LENGTH: 41
<212> TYPE: DNA
<213> ORGANISM: Artificial Sequence
<220> FEATURE:
<223> OTHER INFORMATION: Primer sequence

<400> SEQUENCE: 18
gttctaaaat caggttgttc agcgcttata gtattttgga c        41

<210> SEQ ID NO 19
<211> LENGTH: 44
<212> TYPE: DNA
<213> ORGANISM: Artificial Sequence
<220> FEATURE:
<223> OTHER INFORMATION: Primer sequence

<400> SEQUENCE: 19
ccaaaatact ataagctatg aagcacctga ttttagaaca attc                    44

<210> SEQ ID NO 20
<211> LENGTH: 44
<212> TYPE: DNA
<213> ORGANISM: Artificial Sequence
<220> FEATURE:
<223> OTHER INFORMATION: Primer sequence

<400> SEQUENCE: 20
gaattgttct aaaatcaggt gcttcatagc ttatagtatt ttgg                    44

<210> SEQ ID NO 21
<211> LENGTH: 40
<212> TYPE: DNA
<213> ORGANISM: Artificial Sequence
<220> FEATURE:
<223> OTHER INFORMATION: Primer sequence

<400> SEQUENCE: 21
ctataagcta tgaacaagct gattttagaa caattcaaag                         40

<210> SEQ ID NO 22
<211> LENGTH: 40
<212> TYPE: DNA
<213> ORGANISM: Artificial Sequence
<220> FEATURE:
<223> OTHER INFORMATION: Primer sequence

<400> SEQUENCE: 22
ctttgaattg ttctaaaatc agcttgttca tagcttatag                         40

<210> SEQ ID NO 23
<211> LENGTH: 37
<212> TYPE: DNA
<213> ORGANISM: Artificial Sequence
<220> FEATURE:
<223> OTHER INFORMATION: Primer sequence

<400> SEQUENCE: 23
caattattca tgaaatcagc attgtataat aatggtg                            37

<210> SEQ ID NO 24
<211> LENGTH: 37
<212> TYPE: DNA
<213> ORGANISM: Artificial Sequence
<220> FEATURE:
<223> OTHER INFORMATION: Primer sequence

<400> SEQUENCE: 24
caccattatt atacaatgct gatttcatga ataattg                            37

<210> SEQ ID NO 25
<211> LENGTH: 10
<212> TYPE: PRT
<213> ORGANISM: Artificial Sequence
<220> FEATURE:
<223> OTHER INFORMATION: Mutant peptide fragment

```
<220> FEATURE:
<221> NAME/KEY: Xaa
<222> LOCATION: (5)..(5)
<223> OTHER INFORMATION: Any amino acid other than Y

<400> SEQUENCE: 25

Asn Thr Ile Ser Xaa Glu Gln Pro Asp Phe
1               5                   10

<210> SEQ ID NO 26
<211> LENGTH: 20
<212> TYPE: PRT
<213> ORGANISM: Artificial Sequence
<220> FEATURE:
<223> OTHER INFORMATION: Mutant peptide fragment
<220> FEATURE:
<221> NAME/KEY: Xaa
<222> LOCATION: (10)..(10)
<223> OTHER INFORMATION: Any amino acid other than Y

<400> SEQUENCE: 26

Ser Tyr Asn Val Gln Asn Thr Ile Ser Xaa Glu Gln Pro Asp Phe Arg
1               5                   10                  15

Thr Ile Gln Arg
            20

<210> SEQ ID NO 27
<211> LENGTH: 10
<212> TYPE: PRT
<213> ORGANISM: Artificial Sequence
<220> FEATURE:
<223> OTHER INFORMATION: Mutant peptide fragment
<220> FEATURE:
<221> NAME/KEY: Xaa
<222> LOCATION: (5)..(5)
<223> OTHER INFORMATION: Any amino acid other than P

<400> SEQUENCE: 27

Ala Asn Ser Ile Xaa Lys Asn Thr Ile Asp
1               5                   10

<210> SEQ ID NO 28
<211> LENGTH: 20
<212> TYPE: PRT
<213> ORGANISM: Artificial Sequence
<220> FEATURE:
<223> OTHER INFORMATION: Mutant peptide fragment
<220> FEATURE:
<221> NAME/KEY: Xaa
<222> LOCATION: (10)..(10)
<223> OTHER INFORMATION: any amino acid other than P
<220> FEATURE:
<221> NAME/KEY: Xaa
<222> LOCATION: (10)..(10)
<223> OTHER INFORMATION: Any amino acid other than P

<400> SEQUENCE: 28

Asn Asn Ile Lys Ile Ala Asn Ser Ile Xaa Lys Asn Thr Ile Asp Lys
1               5                   10                  15

Lys Asp Val Ser
            20

<210> SEQ ID NO 29
<211> LENGTH: 68
<212> TYPE: PRT
<213> ORGANISM: Artificial Sequence
<220> FEATURE:
<223> OTHER INFORMATION: Polypeptide fragment
```

<400> SEQUENCE: 29

Asn Asn Asn Ile Lys Ile Ala Asn Ser Ile Pro Lys Asn Thr Ile Asp
1               5                   10                  15

Lys Lys Asp Val Ser Asn Ser Ile Gly Tyr Ser Ile Gly Gly Asn Ile
            20                  25                  30

Ser Val Glu Gly Lys Thr Ala Gly Ala Gly Ile Asn Ala Ser Tyr Asn
        35                  40                  45

Val Gln Asn Thr Ile Ser Tyr Glu Gln Pro Asp Phe Arg Thr Ile Gln
    50                  55                  60

Arg Lys Asp Asp
65

<210> SEQ ID NO 30
<211> LENGTH: 48
<212> TYPE: PRT
<213> ORGANISM: Artificial Sequence
<220> FEATURE:
<223> OTHER INFORMATION: Polypeptide fragment

<400> SEQUENCE: 30

Pro Lys Asn Thr Ile Asp Lys Lys Asp Val Ser Asn Ser Ile Gly Tyr
1               5                   10                  15

Ser Ile Gly Gly Asn Ile Ser Val Glu Gly Lys Thr Ala Gly Ala Gly
            20                  25                  30

Ile Asn Ala Ser Tyr Asn Val Gln Asn Thr Ile Ser Tyr Glu Gln Pro
        35                  40                  45

<210> SEQ ID NO 31
<211> LENGTH: 879
<212> TYPE: DNA
<213> ORGANISM: Artificial Sequence
<220> FEATURE:
<223> OTHER INFORMATION: Mutant encoding DNA

<400> SEQUENCE: 31
agtgaattaa atgacataaa caaaattgag ttgaaaaatc taagtggaga ataataaaa      60 gaaaatggaa aggaagctat taaatatact tctagtgata ccgcttcaca taaaggttgg    120
aaggcaactt taagtggaac atttattgaa gatcctcatt ctgataagaa aactgcttta    180
ttaaatttag aaggatttat accttctgat aaacagattt ttggttctaa atattacgga    240
aaaatgaaat ggcctgaaac ttatagaatt aatgtaaaaa gtgctgatgt aaataataat    300
ataaaaatag caaattctat tcctaaaaat actatagata aaaagatgt atctaattca     360 attggttatt ctataggcgg taatatatct gttgaaggaa aaactgctgg tgctggaata    420
aatgcttcat ataatgtcca aaatactata agcgctgaac aacctgattt tagaacaatt    480
caaagaaaag atgatgcaaa tttagcatca tgggatataa aatttgttga gactaaggac    540
ggttataata tagattctta tcatgctatt tatggaaatc aattattcat gaaatcaaga    600
ttgtataata atggtgataa aaatttcaca gatgatagag atttatcaac attaatttct    660
ggtggatttt cacccaatat ggctttagca ttaacagcac ctaaaaatgc taagaatct     720 gtaataatag ttgaatatca aagatttgat aatgactata tttaaattg ggaaactact     780 caatggcgag gaacaaacaa actttcgtca acaagtgaat ataacgaatt tatgtttaaa    840
ataaattggc aagatcataa aatagaatat tatctgtaa                           879

<210> SEQ ID NO 32
<211> LENGTH: 879

<212> TYPE: DNA
<213> ORGANISM: Artificial Sequence
<220> FEATURE:
<223> OTHER INFORMATION: Mutant encoding DNA

<400> SEQUENCE: 32

```
agtgaattaa atgacataaa caaaattgag ttgaaaaatc taagtggaga aataataaaa     60
gaaaatggaa aggaagctat taaatatact tctagtgata ccgcttcaca taaaggttgg    120
aaggcaactt taagtggaac atttattgaa gatcctcatt ctgataagaa aactgcttta    180
ttaaatttag aaggatttat accttctgat aaacagattt ttggttctaa atattacgga    240
aaaatgaaat ggcctgaaac ttatagaatt aatgtaaaaa gtgctgatgt aaataataat    300
ataaaaatag caaattctat tgctaaaaat actatagata aaaaagatgt atctaattca    360
attggttatt ctataggcgg taatatatct gttgaaggaa aaactgctgg tgctggaata    420
aatgcttcat ataatgtcca aaatactata agctatgaac aacctgattt tagaacaatt    480
caaagaaaag atgatgcaaa tttagcatca tgggatataa aatttgttga gactaaggac    540
ggttataata tagattctta tcatgctatt tatggaaatc aattattcat gaaatcaaga    600
ttgtataata atggtgataa aaatttcaca gatgatagag atttatcaac attaatttct    660
ggtggatttt cacccaatat ggctttagca ttaacagcac ctaaaaatgc taaagaatct    720
gtaataatag ttgaatatca aagatttgat aatgactata ttttaaattg ggaaactact    780
caatggcgag gaacaaacaa actttcgtca acaagtgaat ataacgaatt tatgtttaaa    840
ataaattggc aagatcataa aatagaatat tatctgtaa                           879
```

<210> SEQ ID NO 33
<211> LENGTH: 879
<212> TYPE: DNA
<213> ORGANISM: Artificial Sequence
<220> FEATURE:
<223> OTHER INFORMATION: Encoding mature NetB

<400> SEQUENCE: 33

```
agtgaattaa atgacataaa caaaattgag ttgaaaaatc taagtggaga aataataaaa     60
gaaaatggaa aggaagctat taaatatact tctagtgata ccgcttcaca taaaggttgg    120
aaggcaactt taagtggaac atttattgaa gatcctcatt ctgataagaa aactgcttta    180
ttaaatttag aaggatttat accttctgat aaacagattt ttggttctaa atattacgga    240
aaaatgaaat ggcctgaaac ttatagaatt aatgtaaaaa gtgctgatgt aaataataat    300
ataaaaatag caaattctat tcctaaaaat actatagata aaaaagatgt atctaattca    360
attggttatt ctataggcgg taatatatct gttgaaggaa aaactgctgg tgctggaata    420
aatgcttcat ataatgtcca aaatactata agctatgaac aacctgattt tagaacaatt    480
caaagaaaag atgatgcaaa tttagcatca tgggatataa aatttgttga gactaaggac    540
ggttataata tagattctta tcatgctatt tatggaaatc aattattcat gaaatcaaga    600
ttgtataata atggtgataa aaatttcaca gatgatagag atttatcaac attaatttct    660
ggtggatttt cacccaatat ggctttagca ttaacagcac ctaaaaatgc taaagaatct    720
gtaataatag ttgaatatca aagatttgat aatgactata ttttaaattg ggaaactact    780
caatggcgag gaacaaacaa actttcgtca acaagtgaat ataacgaatt tatgtttaaa    840
ataaattggc aagatcataa aatagaatat tatctgtaa                           879
```

<210> SEQ ID NO 34

```
<211> LENGTH: 86
<212> TYPE: PRT
<213> ORGANISM: Artificial Sequence
<220> FEATURE:
<223> OTHER INFORMATION: Polypeptide fragment

<400> SEQUENCE: 34

Tyr Asn Ile Asp Ser Tyr His Ala Ile Tyr Gly Asn Gln Leu Phe Met
1               5                   10                  15

Lys Ser Arg Leu Tyr Asn Asn Gly Asp Lys Asn Phe Thr Asp Asp Arg
            20                  25                  30

Asp Leu Ser Thr Leu Ile Ser Gly Gly Phe Ser Pro Asn Met Ala Leu
        35                  40                  45

Ala Leu Thr Ala Pro Lys Asn Ala Lys Glu Ser Val Ile Ile Val Glu
    50                  55                  60

Tyr Gln Arg Phe Asp Asn Asp Tyr Ile Leu Asn Trp Glu Thr Thr Gln
65                  70                  75                  80

Trp Arg Gly Thr Asn Lys
                85

<210> SEQ ID NO 35
<211> LENGTH: 76
<212> TYPE: PRT
<213> ORGANISM: Artificial Sequence
<220> FEATURE:
<223> OTHER INFORMATION: Polypeptide fragment

<400> SEQUENCE: 35

Tyr His Ala Ile Tyr Gly Asn Gln Leu Phe Met Lys Ser Arg Leu Tyr
1               5                   10                  15

Asn Asn Gly Asp Lys Asn Phe Thr Asp Asp Arg Asp Leu Ser Thr Leu
            20                  25                  30

Ile Ser Gly Gly Phe Ser Pro Asn Met Ala Leu Ala Leu Thr Ala Pro
        35                  40                  45

Lys Asn Ala Lys Glu Ser Val Ile Ile Val Glu Tyr Gln Arg Phe Asp
    50                  55                  60

Asn Asp Tyr Ile Leu Asn Trp Glu Thr Thr Gln Trp
65                  70                  75

<210> SEQ ID NO 36
<211> LENGTH: 292
<212> TYPE: PRT
<213> ORGANISM: Artificial Sequence
<220> FEATURE:
<223> OTHER INFORMATION: Mutated polypeptide sequence

<400> SEQUENCE: 36

Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95
```

```
Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
            115                 120                 125

Ile Ser Val Glu Gly Lys Thr Ala Gly Ala Gly Ile Asn Ala Ser Tyr
            130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
            165                 170                 175

Glu Thr Lys Asp Gly Tyr Asn Ile Asp Ser Tyr His Ala Ile Ala Gly
            180                 185                 190

Asn Gln Leu Phe Met Lys Ser Arg Leu Tyr Asn Asn Gly Asp Lys Asn
            195                 200                 205

Phe Thr Asp Asp Arg Asp Leu Ser Thr Leu Ile Ser Gly Gly Phe Ser
            210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
            245                 250                 255

Trp Glu Thr Thr Gln Trp Arg Gly Thr Asn Lys Leu Ser Ser Thr Ser
            260                 265                 270

Glu Tyr Asn Glu Phe Met Phe Lys Ile Asn Trp Gln Asp His Lys Ile
            275                 280                 285

Glu Tyr Tyr Leu
            290

<210> SEQ ID NO 37
<211> LENGTH: 292
<212> TYPE: PRT
<213> ORGANISM: Artificial Sequence
<220> FEATURE:
<223> OTHER INFORMATION: Mutated polypeptide sequence

<400> SEQUENCE: 37

Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
            35                  40                  45

Ile Glu Asp Pro His Ser Asp Lys Lys Thr Ala Leu Leu Asn Leu Glu
        50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
            85                  90                  95

Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
            115                 120                 125

Ile Ser Val Glu Gly Lys Thr Ala Gly Ala Gly Ile Asn Ala Ser Tyr
            130                 135                 140

Asn Val Gln Asn Thr Ile Ser Tyr Glu Gln Pro Asp Phe Arg Thr Ile
145                 150                 155                 160
```

```
Gln Arg Lys Asp Asp Ala Asn Leu Ala Ser Trp Asp Ile Lys Phe Val
            165                 170                 175

Glu Thr Lys Asp Gly Tyr Asn Ile Asp Ser Tyr His Ala Ile Tyr Gly
        180                 185                 190

Asn Gln Leu Phe Met Lys Ser Ala Leu Tyr Asn Asn Gly Asp Lys Asn
            195                 200                 205

Phe Thr Asp Asp Arg Asp Leu Ser Thr Leu Ile Ser Gly Gly Phe Ser
210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
                245                 250                 255

Trp Glu Thr Thr Gln Trp Arg Gly Thr Asn Lys Leu Ser Ser Thr Ser
            260                 265                 270

Glu Tyr Asn Glu Phe Met Phe Lys Ile Asn Trp Gln Asp His Lys Ile
        275                 280                 285

Glu Tyr Tyr Leu
    290

<210> SEQ ID NO 38
<211> LENGTH: 292
<212> TYPE: PRT
<213> ORGANISM: Artificial Sequence
<220> FEATURE:
<223> OTHER INFORMATION: Mutated polypeptide sequence

<400> SEQUENCE: 38

Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
        115                 120                 125

Ile Ser Val Glu Gly Lys Thr Ala Gly Ala Gly Ile Asn Ala Ser Tyr
    130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
            180                 185                 190

Asn Gln Leu Phe Met Lys Ser Arg Leu Tyr Asn Asn Gly Asp Lys Asn
        195                 200                 205

Phe Thr Asp Asp Arg Asp Leu Ser Thr Leu Ile Ser Gly Gly Phe Ser
    210                 215                 220
```

```
Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
                245                 250                 255

Ala Glu Thr Thr Gln Trp Arg Gly Thr Asn Lys Leu Ser Ser Thr Ser
            260                 265                 270

Glu Tyr Asn Glu Phe Met Phe Lys Ile Asn Trp Gln Asp His Lys Ile
        275                 280                 285

Glu Tyr Tyr Leu
        290

<210> SEQ ID NO 39
<211> LENGTH: 292
<212> TYPE: PRT
<213> ORGANISM: Artificial Sequence
<220> FEATURE:
<223> OTHER INFORMATION: Mutated polypeptide sequence

<400> SEQUENCE: 39

Ser Glu Leu Asn Asp Ile Asn Lys Ile Glu Leu Lys Asn Leu Ser Gly
1               5                   10                  15

Glu Ile Ile Lys Glu Asn Gly Lys Glu Ala Ile Lys Tyr Thr Ser Ser
            20                  25                  30

Asp Thr Ala Ser His Lys Gly Trp Lys Ala Thr Leu Ser Gly Thr Phe
        35                  40                  45

Ile Glu Asp Pro His Ser Asp Lys Lys Thr Ala Leu Leu Asn Leu Glu
    50                  55                  60

Gly Phe Ile Pro Ser Asp Lys Gln Ile Phe Gly Ser Lys Tyr Tyr Gly
65                  70                  75                  80

Lys Met Lys Trp Pro Glu Thr Tyr Arg Ile Asn Val Lys Ser Ala Asp
                85                  90                  95

Val Asn Asn Asn Ile Lys Ile Ala Asn Ser Ile Pro Lys Asn Thr Ile
            100                 105                 110

Asp Lys Lys Asp Val Ser Asn Ser Ile Gly Tyr Ser Ile Gly Gly Asn
        115                 120                 125

Ile Ser Val Glu Gly Lys Thr Ala Gly Ala Gly Ile Asn Ala Ser Tyr
    130                 135                 140

Asn Val Gln Asn Thr Ile Ser Tyr Glu Gln Pro Asp Phe Arg Thr Ile
145                 150                 155                 160

Gln Arg Lys Asp Asp Ala Asn Leu Ala Ser Trp Asp Ile Lys Phe Val
                165                 170                 175

Glu Thr Lys Asp Gly Tyr Asn Ile Asp Ser Tyr His Ala Ile Tyr Gly
            180                 185                 190

Asn Gln Leu Phe Met Lys Ser Arg Leu Tyr Asn Asn Gly Asp Lys Asn
        195                 200                 205

Phe Thr Asp Asp Arg Asp Leu Ser Thr Leu Ile Ser Gly Gly Phe Ser
    210                 215                 220

Pro Asn Met Ala Leu Ala Leu Thr Ala Pro Lys Asn Ala Lys Glu Ser
225                 230                 235                 240

Val Ile Ile Val Glu Tyr Gln Arg Phe Asp Asn Asp Tyr Ile Leu Asn
                245                 250                 255

Trp Glu Thr Thr Gln Ala Arg Gly Thr Asn Lys Leu Ser Ser Thr Ser
            260                 265                 270

Glu Tyr Asn Glu Phe Met Phe Lys Ile Asn Trp Gln Asp His Lys Ile
        275                 280                 285
```

```
Glu Tyr Tyr Leu
    290

<210> SEQ ID NO 40
<211> LENGTH: 10
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (5)..(5)
<223> OTHER INFORMATION: Any amino acid other than Y
<220> FEATURE:
<221> NAME/KEY: Xaa
<222> LOCATION: (5)..(5)
<223> OTHER INFORMATION: Any amino acid other than Y

<400> SEQUENCE: 40

Tyr His Ala Ile Xaa Gly Asn Gln Leu Phe
1               5                   10

<210> SEQ ID NO 41
<211> LENGTH: 20
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (10)..(10)
<223> OTHER INFORMATION: Any amino acid other than Y
<220> FEATURE:
<221> NAME/KEY: Xaa
<222> LOCATION: (10)..(10)
<223> OTHER INFORMATION: Any amino acid other than Y

<400> SEQUENCE: 41

Tyr Asn Ile Asp Ser Tyr His Ala Ile Xaa Gly Asn Gln Leu Phe Met
1               5                   10                  15

Lys Ser Arg Leu
            20

<210> SEQ ID NO 42
<211> LENGTH: 10
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (5)..(5)
<223> OTHER INFORMATION: Any amino acid other than R
<220> FEATURE:
<221> NAME/KEY: Xaa
<222> LOCATION: (5)..(5)
<223> OTHER INFORMATION: Any amino acid other than R

<400> SEQUENCE: 42

Phe Met Lys Ser Xaa Leu Tyr Asn Asn Gly
1               5                   10

<210> SEQ ID NO 43
<211> LENGTH: 20
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (10)..(10)
```

```
<223> OTHER INFORMATION: Any amino acid other than R
<220> FEATURE:
<221> NAME/KEY: Xaa
<222> LOCATION: (10)..(10)
<223> OTHER INFORMATION: Any amino acid other than R

<400> SEQUENCE: 43

Tyr Gly Asn Gln Leu Phe Met Lys Ser Xaa Leu Tyr Asn Asn Gly Asp
1               5                   10                  15

Lys Asn Phe Thr
            20

<210> SEQ ID NO 44
<211> LENGTH: 10
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (5)..(5)
<223> OTHER INFORMATION: Any amino acid other than W
<220> FEATURE:
<221> NAME/KEY: Xaa
<222> LOCATION: (5)..(5)
<223> OTHER INFORMATION: Any amino acid other than W

<400> SEQUENCE: 44

Tyr Ile Leu Asn Xaa Glu Thr Thr Gln Trp
1               5                   10

<210> SEQ ID NO 45
<211> LENGTH: 20
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (10)..(10)
<223> OTHER INFORMATION: Any amino acid other than W.
<220> FEATURE:
<221> NAME/KEY: Xaa
<222> LOCATION: (10)..(10)
<223> OTHER INFORMATION: Any amino acid other than W.

<400> SEQUENCE: 45

Arg Phe Asp Asn Asp Tyr Ile Leu Asn Xaa Glu Thr Thr Gln Trp Arg
1               5                   10                  15

Gly Thr Asn Lys
            20

<210> SEQ ID NO 46
<211> LENGTH: 10
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (5)..(5)
<223> OTHER INFORMATION: Any amino acid other than W
<220> FEATURE:
<221> NAME/KEY: Xaa
<222> LOCATION: (5)..(5)
<223> OTHER INFORMATION: Any amino acid other than W
<220> FEATURE:
<221> NAME/KEY: Xaa
<222> LOCATION: (5)..(5)
<223> OTHER INFORMATION: Any amino acid other than W
```

<400> SEQUENCE: 46

Glu Thr Thr Gln Xaa Arg Gly Thr Asn Lys
1               5                   10

<210> SEQ ID NO 47
<211> LENGTH: 20
<212> TYPE: PRT
<213> ORGANISM: Artificial Sequence
<220> FEATURE:
<223> OTHER INFORMATION: Mutant peptide fragment
<220> FEATURE:
<221> NAME/KEY: X
<222> LOCATION: (10)..(10)
<223> OTHER INFORMATION: Any amino acid other than W
<220> FEATURE:
<221> NAME/KEY: Xaa
<222> LOCATION: (10)..(10)
<223> OTHER INFORMATION: Any amino acid other than W

<400> SEQUENCE: 47

Tyr Ile Leu Asn Trp Glu Thr Thr Gln Xaa Arg Gly Thr Asn Lys Leu
1               5                   10                  15

Ser Ser Thr Ser
            20

<210> SEQ ID NO 48
<211> LENGTH: 879
<212> TYPE: DNA
<213> ORGANISM: Artificial Sequence
<220> FEATURE:
<223> OTHER INFORMATION: Mutant encoding DNA

<400> SEQUENCE: 48

| | | | | | |
|---|---|---|---|---|---|
| agtgaattaa | atgacataaa | caaaattgag | ttgaaaaatc | taagtggaga | aataataaaa | 60 |
| gaaaatggaa | aggaagctat | taaatatact | tctagtgata | ccgcttcaca | taaaggttgg | 120 |
| aaggcaactt | taagtggaac | atttattgaa | gatcctcatt | ctgataagaa | aactgcttta | 180 |
| ttaaatttag | aaggatttat | accttctgat | aaacagattt | ttggttctaa | atattacgga | 240 |
| aaaatgaaat | ggcctgaaac | ttatagaatt | aatgtaaaaa | gtgctgatgt | aaataataat | 300 |
| ataaaaatag | caaattctat | tcctaaaaat | actatagata | aaaagatgt | atctaattca | 360 |
| attggttatt | ctataggcgg | taatatatct | gttgaaggaa | aaactgctgg | tgctggaata | 420 |
| aatgcttcat | ataatgtcca | aaatactata | agctatgaac | aacctgattt | tagaacaatt | 480 |
| caaagaaaag | atgatgcaaa | tttagcatca | tgggatataa | aatttgttga | gactaaggac | 540 |
| ggttataata | tagattctta | tcatgctatt | gctggaaatc | aattattcat | gaaatcaaga | 600 |
| ttgtataata | atggtgataa | aaatttcaca | gatgatagag | atttatcaac | attaatttct | 660 |
| ggtggatttt | cacccaatat | ggctttagca | ttaacagcac | ctaaaaatgc | taagaatct | 720 |
| gtaataatag | ttgaatatca | aagatttgat | aatgactata | ttttaaattg | ggaaactact | 780 |
| caatggcgag | gaacaaacaa | actttcgtca | acaagtgaat | ataacgaatt | tatgtttaaa | 840 |
| ataaattggc | aagatcataa | aatagaatat | tatctgtaa | | | 879 |

<210> SEQ ID NO 49
<211> LENGTH: 879
<212> TYPE: DNA
<213> ORGANISM: Artificial Sequence
<220> FEATURE:
<223> OTHER INFORMATION: Mutant encoding DNA

<400> SEQUENCE: 49

```
agtgaattaa atgacataaa caaaattgag ttgaaaaatc taagtggaga ataataaaa      60 gaaaatggaa aggaagctat taaatatact tctagtgata ccgcttcaca taaaggttgg    120
aaggcaactt taagtggaac atttattgaa gatcctcatt ctgataagaa aactgcttta    180
ttaaatttag aaggatttat accttctgat aaacagattt ttggttctaa atattacgga    240
aaaatgaaat ggcctgaaac ttatagaatt aatgtaaaaa gtgctgatgt aaataataat    300
ataaaaatag caaattctat tcctaaaaat actatagata aaaagatgt atctaattca     360 attggttatt ctataggcgg taatatatct gttgaaggaa aaactgctgg tgctggaata    420
aatgcttcat ataatgtcca aaatactata agctatgaac aacctgattt tagaacaatt    480
caaagaaaag atgatgcaaa tttagcatca tgggatataa aatttgttga gactaaggac    540
ggttataata tagattctta tcatgctatt tatggaaatc aattattcat gaaatcagca    600
ttgtataata atggtgataa aaatttcaca gatgatagag atttatcaac attaatttct    660
ggtggatttt cacccaatat ggctttagca ttaacagcac ctaaaaatgc taagaatct     720 gtaataatag ttgaatatca aagatttgat aatgactata ttttaaattg ggaaactact    780
caatggcgag gaacaaacaa acttcgtca acaagtgaat ataacgaatt tatgtttaaa    840
ataaattggc aagatcataa aatagaatat tatctgtaa                           879
```

<210> SEQ ID NO 50
<211> LENGTH: 879
<212> TYPE: DNA
<213> ORGANISM: Artificial Sequence
<220> FEATURE:
<223> OTHER INFORMATION: Mutant encoding DNA

<400> SEQUENCE: 50

```
agtgaattaa atgacataaa caaaattgag ttgaaaaatc taagtggaga ataataaaa      60 gaaaatggaa aggaagctat taaatatact tctagtgata ccgcttcaca taaaggttgg    120
aaggcaactt taagtggaac atttattgaa gatcctcatt ctgataagaa aactgcttta    180
ttaaatttag aaggatttat accttctgat aaacagattt ttggttctaa atattacgga    240
aaaatgaaat ggcctgaaac ttatagaatt aatgtaaaaa gtgctgatgt aaataataat    300
ataaaaatag caaattctat tcctaaaaat actatagata aaaagatgt atctaattca     360 attggttatt ctataggcgg taatatatct gttgaaggaa aaactgctgg tgctggaata    420
aatgcttcat ataatgtcca aaatactata agctatgaac aacctgattt tagaacaatt    480
caaagaaaag atgatgcaaa tttagcatca tgggatataa aatttgttga gactaaggac    540
ggttataata tagattctta tcatgctatt tatggaaatc aattattcat gaaatcaaga    600
ttgtataata atggtgataa aaatttcaca gatgatagag atttatcaac attaatttct    660
ggtggatttt cacccaatat ggctttagca ttaacagcac ctaaaaatgc taagaatct     720 gtaataatag ttgaatatca aagatttgat aatgactata ttttaaatgc ggaaactact    780
caatggcgag gaacaaacaa acttcgtca acaagtgaat ataacgaatt tatgtttaaa    840
ataaattggc aagatcataa aatagaatat tatctgtaa                           879
```

<210> SEQ ID NO 51
<211> LENGTH: 879
<212> TYPE: DNA
<213> ORGANISM: Artificial Sequence
<220> FEATURE:
<223> OTHER INFORMATION: Mutant encoding DNA

<400> SEQUENCE: 51

-continued

```
agtgaattaa atgacataaa caaaattgag ttgaaaaatc taagtggaga aataataaaa     60
gaaaatggaa aggaagctat taaatatact tctagtgata ccgcttcaca taaaggttgg    120
aaggcaactt taagtggaac atttattgaa gatcctcatt ctgataagaa aactgcttta    180
ttaaatttag aaggatttat accttctgat aaacagattt ttggttctaa atattacgga    240
aaaatgaaat ggcctgaaac ttatagaatt aatgtaaaaa gtgctgatgt aaataataat    300
ataaaaatag caaattctat tcctaaaaat actatagata aaaaagatgt atctaattca    360
attggttatt ctataggcgg taatatatct gttgaaggaa aaactgctgg tgctggaata    420
aatgcttcat ataatgtcca aaatactata agctatgaac aacctgattt tagaacaatt    480
caaagaaaag atgatgcaaa tttagcatca tgggatataa aatttgttga gactaaggac    540
ggttataata tagattctta tcatgctatt tatggaaatc aattattcat gaaatcaaga    600
ttgtataata atggtgataa aaatttcaca gatgatagag atttatcaac attaatttct    660
ggtggatttt cacccaatat ggctttagca ttaacagcac ctaaaaatgc taaagaatct    720
gtaataatag ttgaatatca aagatttgat aatgactata ttttaaattg ggaaactact    780
caagcgcgag gaacaaacaa actttcgtca acaagtgaat ataacgaatt tatgtttaaa    840
ataaattggc aagatcataa aatagaatat tatctgtaa                           879
```